US011672693B2

(12) United States Patent
Hilton et al.

(10) Patent No.: US 11,672,693 B2
(45) Date of Patent: Jun. 13, 2023

(54) INTEGRATED MULTISECTIONAL HEAT EXCHANGER

(71) Applicant: Avent, Inc., Alpharetta, GA (US)

(72) Inventors: Tamara L. Hilton, Alameda, CA (US); Mark H. Lowe, Danville, CA (US); Bryan D. Huff, Vacaville, CA (US)

(73) Assignee: Avent, Inc., Alpharetta, GA (US)

( * ) Notice: Subject to any disclaimer, the term of this patent is extended or adjusted under 35 U.S.C. 154(b) by 719 days.

(21) Appl. No.: 16/178,467

(22) Filed: Nov. 1, 2018

(65) Prior Publication Data

US 2019/0133817 A1    May 9, 2019

Related U.S. Application Data

(63) Continuation of application No. 14/819,276, filed on Aug. 5, 2015, now abandoned.
(Continued)

(51) Int. Cl.
*A61F 7/02* (2006.01)
*A61F 5/055* (2006.01)
*A61F 7/00* (2006.01)

(52) U.S. Cl.
CPC ............... *A61F 7/02* (2013.01); *A61F 5/055* (2013.01); *A61F 2007/0011* (2013.01);
(Continued)

(58) Field of Classification Search
CPC ............. A61F 7/02; A61F 2007/0011; A61F 2007/0054; A61F 2007/0055; A61F 2007/0091; A61F 2007/022; A61F 2007/0225; A61F 2007/025; A61F 2007/0277; A61F 2007/0279; A61F 2007/0268; A61F 2007/0269; A61F 2007/0273; A61F 2007/0274; A61F 2007/0233; A61F 2007/0056; A61F 5/055; A61F 5/05816; A61F 5/012; A61H 9/005; A61H 9/0078; A61H 9/0085;
(Continued)

(56) References Cited

U.S. PATENT DOCUMENTS 1,886,768 A     11/1932   Watson
1,958,899 A     5/1934    MacAdams
(Continued)

FOREIGN PATENT DOCUMENTS

CN        2304378 Y      1/1999
CN        1373649 A      10/2002
(Continued)

OTHER PUBLICATIONS

Shunt definition, entry 2 of 2: definition 1c, https://www.merriam-webster.com/dictionary/shunt (Year: 2021).*
(Continued)

*Primary Examiner* — Ophelia A Hawthorne
*Assistant Examiner* — Michael Milo
(74) *Attorney, Agent, or Firm* — Meunier Carlin & Curfman LLC

(57) ABSTRACT

A multi-sectional therapy wrap can include a first wrap section joined to a second wrap section through a specialized junction that allows the wrap sections to overlap. The junction can also be divided into two portions to facilitate fluid flow between one wrap section and the other wrap section.

18 Claims, 18 Drawing Sheets

Related U.S. Application Data

(60) Provisional application No. 62/033,569, filed on Aug. 5, 2014, provisional application No. 62/057,091, filed on Sep. 29, 2014.

(52) U.S. Cl.
CPC ............... *A61F 2007/0054* (2013.01); *A61F 2007/0225* (2013.01); *A61F 2007/0269* (2013.01)

(58) Field of Classification Search
CPC .......... A61H 9/0092; A61H 2201/0103; A61H 2201/0242; A61H 2201/1604; A61H 2201/1607; A61H 2201/1609; A61H 2201/1611; A61H 2201/1614; A61H 2201/1616

See application file for complete search history.

(56) References Cited

U.S. PATENT DOCUMENTS

| | | |
|---|---|---|
| 2,146,622 A | 2/1939 | Carlo |
| 2,148,661 A | 2/1939 | Thierer |
| 2,413,386 A | 12/1946 | Schulz |
| 2,510,125 A | 6/1950 | Meakin |
| 2,531,074 A | 11/1950 | Miller |
| 2,540,547 A | 2/1951 | Rodert |
| 2,608,690 A | 9/1952 | Kolb et al. |
| 2,703,770 A | 3/1955 | Melzer |
| 2,726,658 A | 12/1955 | Chessey |
| 2,954,898 A | 10/1960 | Feeberg |
| 3,261,042 A | 7/1966 | Baker |
| 3,320,682 A | 5/1967 | Sliman |
| 3,354,898 A | 11/1967 | Barnes |
| 3,559,640 A | 2/1971 | Beckett |
| 3,561,435 A | 2/1971 | Nicholson |
| 3,738,367 A | 6/1973 | Hardy |
| 3,744,555 A | 7/1973 | Fletcher et al. |
| 3,830,676 A | 8/1974 | Elkins |
| 3,867,939 A * | 2/1975 | Moore .................. A61F 7/02 607/104 |
| 3,871,381 A | 3/1975 | Roslonski |
| 3,901,225 A | 8/1975 | Sconce |
| 3,993,053 A | 11/1976 | Grossan |
| 4,020,209 A | 4/1977 | Yuan |
| 4,026,299 A | 5/1977 | Sauder |
| 4,116,476 A | 9/1978 | Porter et al. |
| 4,118,946 A | 10/1978 | Tubin |
| 4,147,921 A | 4/1979 | Walter et al. |
| 4,149,529 A | 4/1979 | Copeland et al. |
| 4,149,541 A | 4/1979 | Gammons et al. |
| 4,170,998 A | 10/1979 | Sauder |
| 4,184,537 A | 1/1980 | Sauder |
| 4,194,247 A | 3/1980 | Melander |
| 4,206,751 A * | 6/1980 | Schneider ............ A61H 9/0078 601/152 |
| 4,320,746 A | 3/1982 | Arkans et al. |
| 4,335,726 A | 6/1982 | Kolstedt |
| 4,338,944 A | 7/1982 | Arkans |
| D269,379 S | 6/1983 | Bledsoe |
| 4,407,276 A | 10/1983 | Bledsoe |
| 4,412,648 A | 11/1983 | Ford et al. |
| 4,436,125 A | 3/1984 | Blenkush |
| 4,441,504 A | 4/1984 | Peterson et al. |
| 4,460,085 A | 7/1984 | Jantzen |
| 4,463,751 A | 8/1984 | Bledsoe |
| 4,471,759 A | 9/1984 | Anderson et al. |
| 4,478,436 A | 10/1984 | Hashimoto |
| 4,547,906 A | 10/1985 | Nishida |
| 4,550,828 A | 11/1985 | Baldwin et al. |
| 4,597,384 A | 7/1986 | Whitney |
| 4,678,027 A | 7/1987 | Shirey et al. |
| 4,691,762 A | 9/1987 | Elkins et al. |
| 4,699,613 A | 10/1987 | Donawick et al. |
| 4,718,429 A | 1/1988 | Smidt |
| 4,738,119 A | 4/1988 | Zafred |
| 4,753,268 A | 6/1988 | Palau |
| 4,765,338 A | 8/1988 | Turner et al. |
| 4,817,588 A | 4/1989 | Bledsoe |
| 4,834,073 A | 5/1989 | Bledsoe et al. |
| 4,844,072 A | 7/1989 | French et al. |
| 4,884,304 A | 12/1989 | Elkins |
| 4,925,603 A | 5/1990 | Nambu |
| 4,955,369 A | 9/1990 | Bledsoe et al. |
| 4,955,435 A | 9/1990 | Shuster et al. |
| 4,962,761 A | 10/1990 | Golden |
| 4,964,282 A | 10/1990 | Wagner |
| 4,964,402 A | 10/1990 | Grim et al. |
| 4,966,145 A | 10/1990 | Kikumoto et al. |
| 4,976,262 A | 12/1990 | Palmacci |
| 5,002,270 A | 3/1991 | Shine |
| 5,014,695 A | 5/1991 | Benak et al. |
| 5,022,109 A | 6/1991 | Pekar |
| 5,033,136 A | 7/1991 | Elkins |
| 5,052,725 A | 10/1991 | Meyer et al. |
| 5,056,563 A | 10/1991 | Glossop |
| 5,072,875 A | 12/1991 | Zacoi |
| 5,074,285 A | 12/1991 | Wright |
| 5,076,068 A | 12/1991 | Mikhail |
| 5,080,089 A | 1/1992 | Mason et al. |
| 5,080,166 A | 1/1992 | Haugeneder |
| 5,086,771 A | 2/1992 | Molloy |
| 5,097,829 A | 3/1992 | Quisenberry |
| 5,104,158 A | 4/1992 | Meyer et al. |
| 5,112,045 A | 5/1992 | Mason et al. |
| 5,113,877 A | 5/1992 | Johnson, Jr. et al. |
| 5,163,425 A | 11/1992 | Nambu et al. |
| 5,163,923 A | 11/1992 | Donawick et al. |
| 5,172,689 A | 12/1992 | Wright |
| 5,186,698 A | 2/1993 | Mason et al. |
| 5,201,552 A | 4/1993 | Hohmann et al. |
| 5,230,335 A | 7/1993 | Johnson, Jr. et al. |
| 5,232,020 A | 8/1993 | Mason et al. |
| 5,241,951 A | 9/1993 | Mason et al. |
| 5,243,706 A | 9/1993 | Frim et al. |
| 5,269,369 A | 12/1993 | Faghri |
| D345,609 S | 3/1994 | Mason et al. |
| 5,294,156 A | 3/1994 | Kumazaki et al. |
| D345,802 S | 4/1994 | Mason et al. |
| D345,803 S | 4/1994 | Mason et al. |
| 5,303,716 A | 4/1994 | Mason et al. |
| 5,305,712 A | 4/1994 | Goldstein |
| 5,314,455 A | 5/1994 | Johnson, Jr. et al. |
| 5,316,250 A | 5/1994 | Mason et al. |
| 5,316,547 A | 5/1994 | Gildersleeve |
| D348,106 S | 6/1994 | Mason et al. |
| 5,324,319 A | 6/1994 | Mason et al. |
| D348,518 S | 7/1994 | Mason et al. |
| D351,472 S | 10/1994 | Mason et al. |
| 5,352,174 A | 10/1994 | Mason et al. |
| 5,353,605 A | 10/1994 | Naaman |
| 5,354,101 A | 10/1994 | Anderson, Jr. |
| 5,354,103 A | 10/1994 | Torrence et al. |
| D352,781 S | 11/1994 | Mason et al. |
| 5,372,575 A | 12/1994 | Sebastian |
| 5,383,689 A | 1/1995 | Wolfe, Sr. |
| 5,383,919 A | 1/1995 | Kelly et al. |
| RE34,883 E | 3/1995 | Grim |
| 5,395,399 A | 3/1995 | Rosenwald |
| 5,407,421 A | 4/1995 | Goldsmith |
| 5,411,541 A * | 5/1995 | Bell .................. A61F 7/02 607/104 |
| 5,415,625 A | 5/1995 | Cassford et al. |
| 5,417,720 A | 5/1995 | Mason |
| 5,427,577 A | 6/1995 | Picchietti et al. |
| 5,441,533 A | 8/1995 | Johnson et al. |
| 5,449,379 A | 9/1995 | Hadtke |
| 5,451,201 A | 9/1995 | Prengler |
| 5,466,250 A | 11/1995 | Johnson, Jr. et al. |
| 5,468,220 A | 11/1995 | Sucher |
| 5,470,353 A | 11/1995 | Jensen |
| 5,476,489 A | 12/1995 | Koewler |
| 5,484,448 A | 1/1996 | Steele et al. |

(56) References Cited

U.S. PATENT DOCUMENTS

| | | |
|---|---|---|
| 5,494,074 A | 2/1996 | Ramacier, Jr. et al. |
| 5,496,358 A | 3/1996 | Rosenwald |
| 5,507,792 A | 4/1996 | Mason et al. |
| 5,509,894 A | 4/1996 | Mason et al. |
| 5,514,081 A | 5/1996 | Mann |
| 5,520,622 A | 5/1996 | Bastyr et al. |
| 5,524,293 A | 6/1996 | Kung |
| 5,527,268 A | 6/1996 | Gildersleeve et al. |
| 5,533,354 A | 7/1996 | Pirkle |
| 5,539,934 A | 7/1996 | Ponder |
| D372,534 S | 8/1996 | Andrews et al. |
| 5,553,712 A | 9/1996 | Tisbo et al. |
| 5,554,119 A | 9/1996 | Harrison et al. |
| 5,556,138 A | 9/1996 | Nakajima et al. |
| 5,564,124 A | 10/1996 | Elsherif et al. |
| 5,569,172 A | 10/1996 | Padden et al. |
| 5,592,694 A | 1/1997 | Yewer |
| 5,609,620 A | 3/1997 | Daily |
| 5,630,328 A | 5/1997 | Hise et al. |
| 5,634,940 A | 6/1997 | Panyard |
| 5,638,707 A | 6/1997 | Gould |
| 5,645,671 A | 7/1997 | Tillinghast |
| D382,113 S | 8/1997 | DuRapau |
| D383,547 S | 9/1997 | Mason et al. |
| D383,848 S | 9/1997 | Mason et al. |
| 5,662,239 A | 9/1997 | Heuvelman |
| 5,662,695 A | 9/1997 | Mason et al. |
| 5,672,152 A | 9/1997 | Mason et al. |
| 5,683,118 A | 11/1997 | Slocum |
| 5,716,388 A | 2/1998 | Petelle |
| 5,728,058 A | 3/1998 | Ouellette et al. |
| 5,732,464 A | 3/1998 | Lamont |
| 5,755,275 A | 5/1998 | Rose et al. |
| 5,755,755 A | 5/1998 | Panyard |
| 5,769,801 A | 6/1998 | Tumey et al. |
| 5,772,618 A | 6/1998 | Mason et al. |
| 5,782,780 A | 7/1998 | Mason et al. |
| 5,792,216 A | 8/1998 | Kappel |
| 5,807,294 A | 9/1998 | Cawley et al. |
| 5,827,208 A | 10/1998 | Mason et al. |
| 5,833,638 A | 11/1998 | Nelson |
| 5,862,675 A | 1/1999 | Scaringe et al. |
| 5,865,841 A | 2/1999 | Kolen et al. |
| 5,866,219 A | 2/1999 | McClure et al. |
| 5,868,690 A | 2/1999 | Eischen, Sr. |
| 5,871,526 A | 2/1999 | Gibbs et al. |
| 5,895,418 A | 4/1999 | Saringer |
| 5,913,885 A | 6/1999 | Klatz et al. |
| 5,920,934 A | 7/1999 | Hannagan et al. |
| 5,951,598 A | 9/1999 | Bishay et al. |
| 5,967,225 A | 10/1999 | Jenkins |
| 5,968,072 A | 10/1999 | Hite et al. |
| 5,970,519 A | 10/1999 | Weber |
| 5,980,561 A | 11/1999 | Kolen et al. |
| 5,984,885 A | 11/1999 | Gaylord, Jr. et al. |
| 5,989,285 A | 11/1999 | DeVilbiss et al. |
| 5,992,459 A | 11/1999 | Sugita et al. |
| 5,997,495 A | 12/1999 | Cook et al. |
| 6,030,412 A | 2/2000 | Klatz et al. |
| 6,036,107 A | 3/2000 | Aspen et al. |
| 6,036,718 A | 3/2000 | Ledford et al. |
| 6,048,326 A | 4/2000 | Davis et al. |
| 6,053,169 A | 4/2000 | Hunt |
| 6,055,670 A | 5/2000 | Parker |
| 6,058,508 A | 5/2000 | Brown Honeysuckle |
| 6,074,413 A | 6/2000 | Davis et al. |
| 6,083,256 A | 7/2000 | Der Ovanesian |
| 6,089,593 A | 7/2000 | Hanson et al. |
| D430,288 S | 8/2000 | Mason et al. |
| D430,289 S | 8/2000 | Mason et al. |
| 6,105,382 A | 8/2000 | Reason |
| 6,109,338 A | 8/2000 | Butzer |
| 6,117,164 A | 9/2000 | Gildersleeve et al. |
| 6,146,347 A | 11/2000 | Porrata |
| 6,146,413 A | 11/2000 | Harman |
| 6,156,059 A | 12/2000 | Olofsson |
| 6,178,562 B1 | 1/2001 | Elkins |
| 6,228,106 B1 | 5/2001 | Simbruner et al. |
| 6,238,427 B1 | 5/2001 | Matta |
| 6,254,554 B1 | 7/2001 | Turtzo |
| 6,260,890 B1 | 7/2001 | Mason |
| 6,261,314 B1 | 7/2001 | Rich |
| 6,270,481 B1 | 8/2001 | Mason et al. |
| 6,306,112 B2 | 10/2001 | Bird |
| 6,328,276 B1 | 12/2001 | Falch et al. |
| 6,349,412 B1 | 2/2002 | Dean |
| 6,352,550 B1 | 3/2002 | Giidersleeve et al. |
| 6,354,635 B1 | 3/2002 | Dyson et al. |
| 6,361,514 B1 | 3/2002 | Brown et al. |
| 6,368,357 B1 | 4/2002 | Schon et al. |
| 6,371,976 B1 | 4/2002 | Vrzalik et al. |
| 6,382,678 B1 | 5/2002 | Field et al. |
| 6,398,748 B1 | 6/2002 | Wilson |
| 6,405,080 B1 | 6/2002 | Lasersohn et al. |
| 6,406,445 B1 | 6/2002 | Ben-nun |
| 6,440,159 B1 | 8/2002 | Edwards et al. |
| 6,443,498 B1 | 9/2002 | Liao |
| 6,508,831 B1 | 1/2003 | Kushnir |
| 6,547,284 B2 | 4/2003 | Rose et al. |
| 6,551,264 B1 | 4/2003 | Cawley et al. |
| 6,551,347 B1 | 4/2003 | Elkins |
| 6,551,348 B1 | 4/2003 | Blalock et al. |
| 6,620,187 B2 | 9/2003 | Carson et al. |
| 6,641,601 B1 | 11/2003 | Augustine et al. |
| 6,645,232 B2 | 11/2003 | Carson |
| 6,660,027 B2 | 12/2003 | Gruszecki et al. |
| D486,870 S | 2/2004 | Mason |
| 6,695,872 B2 | 2/2004 | Elkins |
| 6,699,267 B2 | 3/2004 | Voorhees et al. |
| 6,719,713 B2 | 4/2004 | Mason |
| 6,719,728 B2 | 4/2004 | Mason et al. |
| 6,802,823 B2 | 10/2004 | Mason |
| 6,818,012 B2 | 11/2004 | Ellingboe |
| 6,823,682 B1 | 11/2004 | Jenkins et al. |
| 6,871,878 B2 | 3/2005 | Miros |
| 6,893,414 B2 | 5/2005 | Goble et al. |
| 6,926,311 B2 | 8/2005 | Chang et al. |
| 6,932,304 B1 | 8/2005 | Villamar |
| 6,936,019 B2 | 8/2005 | Mason |
| 6,942,015 B1 | 9/2005 | Jenkins |
| 6,948,501 B2 | 9/2005 | Rastegar et al. |
| 7,008,445 B2 | 3/2006 | Lennox |
| 7,017,213 B2 | 3/2006 | Chisari |
| 7,025,709 B2 | 4/2006 | Riggall |
| 7,059,329 B2 | 6/2006 | Mason et al. |
| 7,060,045 B2 | 6/2006 | Mason et al. |
| 7,060,086 B2 | 6/2006 | Wilson et al. |
| 7,093,903 B2 | 8/2006 | O'Connor et al. |
| 7,107,629 B2 | 9/2006 | Miros et al. |
| 7,108,664 B2 | 9/2006 | Mason et al. |
| 7,117,569 B2 | 10/2006 | Bledsoe |
| 7,125,417 B2 | 10/2006 | Mizrahi |
| 7,141,131 B2 | 11/2006 | Foxen et al. |
| 7,156,054 B1 | 1/2007 | York |
| 7,166,083 B2 | 1/2007 | Bledsoe |
| 7,191,798 B2 | 3/2007 | Edelman et al. |
| 7,198,093 B1 | 4/2007 | Elkins |
| 7,235,059 B2 | 6/2007 | Mason et al. |
| 7,244,239 B2 | 7/2007 | Howard |
| 7,306,568 B2 | 12/2007 | Diana |
| 7,308,304 B2 | 12/2007 | Hampton et al. |
| 7,326,196 B2 | 2/2008 | Olsen et al. |
| 7,418,755 B2 | 9/2008 | Bledsoe et al. |
| 7,434,844 B2 | 10/2008 | Kao |
| 7,448,653 B2 | 11/2008 | Jensen et al. |
| 7,479,122 B2 | 1/2009 | Ceriani et al. |
| 7,485,103 B2 | 2/2009 | Mason et al. |
| 7,490,620 B2 | 2/2009 | Tesluk et al. |
| 7,500,957 B2 | 3/2009 | Bledsoe |
| 7,640,764 B2 | 1/2010 | Gammons et al. |
| 7,658,205 B1 | 2/2010 | Edelman et al. |
| 7,694,693 B1 | 4/2010 | Edelman et al. |
| 7,731,244 B2 | 6/2010 | Miros et al. |
| 7,785,283 B1 | 8/2010 | Bledsoe |

(56) References Cited

U.S. PATENT DOCUMENTS

| | | |
|---|---|---|
| 7,833,184 B2 | 11/2010 | Chiodo et al. |
| 7,837,638 B2 | 11/2010 | Miros et al. |
| 7,864,941 B1 | 1/2011 | Bledsoe et al. |
| 7,871,427 B2 | 1/2011 | Dunbar et al. |
| 7,896,910 B2 | 3/2011 | Schirrmacher et al. |
| 7,908,692 B2 | 3/2011 | Lange |
| 7,914,563 B2 | 3/2011 | Mason et al. |
| 7,959,588 B1 | 6/2011 | Wolpa |
| 7,988,653 B2 | 8/2011 | Fout et al. |
| 8,016,779 B2 | 9/2011 | Brown et al. |
| 8,052,628 B1 | 11/2011 | Edelman et al. |
| 8,066,752 B2 | 11/2011 | Hamilton et al. |
| 8,109,273 B2 | 2/2012 | Golden et al. |
| 8,182,521 B2 | 5/2012 | Kane et al. |
| 8,216,163 B2 | 7/2012 | Edelman |
| 8,216,290 B2 | 7/2012 | Shawver et al. |
| 8,216,398 B2 | 7/2012 | Bledsoe et al. |
| 8,226,698 B2 | 7/2012 | Edelman et al. |
| 8,251,932 B2 | 8/2012 | Fout |
| 8,251,936 B2 | 8/2012 | Fout et al. |
| 8,273,045 B2 | 9/2012 | Ceriani |
| 8,277,403 B2 | 10/2012 | Ceriani et al. |
| 8,328,742 B2 | 12/2012 | Bledsoe |
| 8,414,512 B2 | 4/2013 | Fout |
| 8,419,670 B2 | 4/2013 | Downing |
| 8,425,579 B1 | 4/2013 | Edelman et al. |
| 8,444,581 B1 | 5/2013 | Maxon-Maldonado et al. |
| 8,512,263 B2 | 8/2013 | Gammons |
| 8,597,217 B2 | 12/2013 | Lowe et al. |
| 8,613,762 B2 | 12/2013 | Bledsoe |
| 8,715,330 B2 | 5/2014 | Lowe et al. |
| 9,132,057 B2 | 9/2015 | Wilford et al. |
| 9,615,967 B2 | 4/2017 | Lowe et al. |
| 9,943,437 B2 | 4/2018 | Lowe et al. |
| 9,980,844 B2 | 5/2018 | Miros et al. |
| 2001/0018604 A1 | 8/2001 | Elkins |
| 2001/0034545 A1 | 10/2001 | Elkins |
| 2001/0034546 A1 | 10/2001 | Elkins |
| 2001/0039439 A1 | 11/2001 | Elkins et al. |
| 2002/0019657 A1 | 2/2002 | Elkins |
| 2002/0026226 A1 | 2/2002 | Ein |
| 2002/0032473 A1 | 3/2002 | Kushnir et al. |
| 2002/0041621 A1 | 4/2002 | Faries et al. |
| 2002/0058975 A1 | 5/2002 | Bieberich |
| 2002/0082668 A1 | 6/2002 | Ingman |
| 2002/0093189 A1 | 7/2002 | Krupa |
| 2002/0108279 A1 | 8/2002 | Hubbard et al. |
| 2003/0060761 A1 | 3/2003 | Evans et al. |
| 2003/0196352 A1 | 10/2003 | Bledsoe et al. |
| 2004/0064170 A1 | 4/2004 | Radons et al. |
| 2004/0064171 A1 | 4/2004 | Briscoe et al. |
| 2004/0068309 A1 | 4/2004 | Edelman |
| 2004/0158303 A1 | 8/2004 | Lennox et al. |
| 2004/0167594 A1 | 8/2004 | Elkins |
| 2004/0210283 A1 | 10/2004 | Rose et al. |
| 2004/0225341 A1 | 11/2004 | Schock et al. |
| 2004/0243202 A1 | 12/2004 | Lennox |
| 2005/0027173 A1 | 2/2005 | Briscoe et al. |
| 2005/0065581 A1 | 3/2005 | Fletcher et al. |
| 2005/0126578 A1 | 6/2005 | Garrison et al. |
| 2005/0131324 A1 | 6/2005 | Bledsoe |
| 2005/0136213 A1 | 6/2005 | Seth et al. |
| 2005/0143796 A1 | 6/2005 | Augustine et al. |
| 2005/0143797 A1 | 6/2005 | Parish et al. |
| 2006/0058858 A1 | 3/2006 | Smith |
| 2006/0069418 A1 | 3/2006 | Schock et al. |
| 2006/0144557 A1 | 7/2006 | Koscheyev et al. |
| 2006/0190062 A1 | 8/2006 | Worthen |
| 2006/0200057 A1 | 9/2006 | Sterling |
| 2006/0287697 A1 | 12/2006 | Lennox |
| 2007/0060987 A1 | 3/2007 | Grahn et al. |
| 2007/0068651 A1 | 3/2007 | Gammons et al. |
| 2007/0108829 A1 | 5/2007 | Lehn et al. |
| 2007/0118194 A1 | 5/2007 | Mason et al. |
| 2007/0118965 A1 | 5/2007 | Hoffman |
| 2007/0157931 A1 | 7/2007 | Parker et al. |
| 2007/0161932 A1 | 7/2007 | Pick et al. |
| 2007/0161933 A1 | 7/2007 | Ravikumar |
| 2007/0167895 A1 | 7/2007 | Gramza et al. |
| 2007/0191918 A1 | 8/2007 | MacHold et al. |
| 2007/0282230 A1 | 12/2007 | Valderrabano et al. |
| 2008/0000474 A1 | 1/2008 | Jochle et al. |
| 2008/0058911 A1 | 3/2008 | Parish et al. |
| 2008/0065172 A1 | 3/2008 | Magdych |
| 2008/0067095 A1 | 3/2008 | Mueller |
| 2008/0097560 A1 | 4/2008 | Radziunas et al. |
| 2008/0097561 A1 | 4/2008 | Melsky et al. |
| 2008/0132816 A1 | 6/2008 | Kane et al. |
| 2008/0132976 A1 | 6/2008 | Kane et al. |
| 2008/0161891 A1 | 7/2008 | Pierre et al. |
| 2008/0234788 A1 | 9/2008 | Wasowski |
| 2008/0249593 A1 | 10/2008 | Cazzini et al. |
| 2008/0269852 A1 | 10/2008 | Lennox et al. |
| 2008/0275534 A1 | 11/2008 | Noel |
| 2008/0283426 A1 | 11/2008 | Primer et al. |
| 2009/0005841 A1 | 1/2009 | Schirrmacher et al. |
| 2009/0018623 A1 | 1/2009 | Levinson et al. |
| 2009/0038195 A1 | 2/2009 | Riker et al. |
| 2009/0062890 A1 | 3/2009 | Ugajin et al. |
| 2009/0069731 A1 | 3/2009 | Parish et al. |
| 2009/0183410 A1 | 7/2009 | Tursso et al. |
| 2010/0006631 A1 | 1/2010 | Edwards et al. |
| 2010/0076531 A1 | 3/2010 | Beran et al. |
| 2010/0089896 A1 | 4/2010 | Bart |
| 2010/0094187 A1 | 4/2010 | Murinson et al. |
| 2010/0137951 A1 | 6/2010 | Lennox et al. |
| 2010/0137953 A1 | 6/2010 | Stein |
| 2010/0139294 A1 | 6/2010 | Lowe et al. |
| 2010/0145421 A1 | 6/2010 | Tomlinson et al. |
| 2010/0161013 A1 | 6/2010 | Heaton |
| 2010/0217349 A1 | 8/2010 | Fahey |
| 2010/0241120 A1 | 9/2010 | Bledsoe et al. |
| 2011/0004132 A1 | 1/2011 | Cook |
| 2011/0040359 A1 | 2/2011 | Harris et al. |
| 2011/0046700 A1 | 2/2011 | McDonald et al. |
| 2011/0087142 A1 | 4/2011 | Ravikumar et al. |
| 2011/0098792 A1 | 4/2011 | Lowe et al. |
| 2011/0106023 A1 | 5/2011 | Lowe |
| 2011/0152982 A1 | 6/2011 | Richardson |
| 2011/0152983 A1 | 6/2011 | Schirrmacher et al. |
| 2011/0172749 A1 | 7/2011 | Christensen et al. |
| 2011/0307038 A1 | 12/2011 | Stiehr |
| 2012/0010546 A1 | 1/2012 | Sotereanos et al. |
| 2012/0028764 A1 | 2/2012 | Miller |
| 2012/0143111 A1 | 6/2012 | Bledsoe et al. |
| 2012/0172774 A1* | 7/2012 | Lowe .................. A61F 7/02 156/291 |
| 2012/0172955 A1 | 7/2012 | Dewaegenaere |
| 2012/0179084 A1 | 7/2012 | Lipshaw et al. |
| 2012/0233736 A1 | 9/2012 | Tepper et al. |
| 2012/0245483 A1 | 9/2012 | Lundqvist |
| 2012/0288848 A1* | 11/2012 | Latham .................. A61F 7/02 604/113 |
| 2012/0330199 A1 | 12/2012 | Lurie et al. |
| 2012/0330202 A1* | 12/2012 | Flick .................. A61F 7/02 602/14 |
| 2013/0006154 A1 | 1/2013 | Lowe |
| 2013/0006335 A1 | 1/2013 | Lowe |
| 2013/0012847 A1 | 1/2013 | Lowe et al. |
| 2013/0013033 A1 | 1/2013 | Lowe |
| 2013/0090683 A1 | 4/2013 | Schock |
| 2013/0123890 A1 | 5/2013 | Latham |
| 2013/0165847 A1 | 6/2013 | Scarpaci et al. |
| 2013/0190553 A1 | 7/2013 | Wong et al. |
| 2013/0245519 A1 | 9/2013 | Edelman et al. |
| 2013/0245729 A1 | 9/2013 | Edelman et al. |
| 2013/0296981 A1* | 11/2013 | Saggers .................. A61F 7/0085 607/104 |
| 2014/0012169 A1* | 1/2014 | Wilford .................. A61H 1/008 601/151 |
| 2014/0074198 A1 | 3/2014 | Bledsoe |
| 2014/0078086 A1 | 3/2014 | Bledsoe et al. |
| 2014/0222121 A1 | 8/2014 | Spence et al. |
| 2014/0236256 A1 | 8/2014 | Rossing |

(56) References Cited

U.S. PATENT DOCUMENTS

| | | |
|---|---|---|
| 2014/0277301 A1 | 9/2014 | Varga et al. |
| 2014/0316314 A1 | 10/2014 | Schubert |
| 2015/0150717 A1 | 6/2015 | Lowe et al. |
| 2015/0224015 A1* | 8/2015 | Wilford .................. A61F 7/02 601/151 |
| 2015/0320588 A1 | 11/2015 | Connor |
| 2015/0335468 A1 | 11/2015 | Rose et al. |
| 2015/0374538 A1 | 12/2015 | Rogers |
| 2016/0030234 A1 | 2/2016 | Lofy et al. |
| 2016/0038336 A1 | 2/2016 | Schirrmacher et al. |
| 2016/0128865 A1 | 5/2016 | Lowe |
| 2016/0166428 A1 | 6/2016 | Hilton et al. |
| 2017/0216129 A1 | 8/2017 | Lowe et al. |
| 2018/0207025 A1 | 7/2018 | Lowe et al. |
| 2018/0271688 A1 | 9/2018 | Miros et al. |

FOREIGN PATENT DOCUMENTS

| | | |
|---|---|---|
| CN | 2880025 Y | 3/2007 |
| CN | 201001805 Y | 1/2008 |
| CN | 201070419 Y | 6/2008 |
| CN | 101524301 A | 9/2009 |
| DE | 3343664 C1 | 3/1985 |
| DE | 29716336 U1 | 1/1998 |
| DE | 29716338 U1 | 1/1998 |
| EP | 0344949 A2 | 12/1989 |
| EP | 0412708 A1 | 2/1991 |
| EP | 0535830 A1 | 4/1993 |
| EP | 0861651 B1 | 4/2002 |
| EP | 1329676 A1 | 7/2003 |
| EP | 1393751 A1 | 3/2004 |
| EP | 1972312 A2 | 9/2008 |
| FR | 819022 A | 10/1937 |
| IT | 330552 | 10/1935 |
| JP | 08-229061 A | 9/1996 |
| JP | 2000288007 A | 10/2000 |
| KR | 20-0153967 | 8/1999 |
| KR | 100654317 B1 | 12/2006 |
| NL | 2011288 C | 9/2013 |
| WO | 92/13506 A1 | 8/1992 |
| WO | 92/15263 A1 | 9/1992 |
| WO | 94/09732 A1 | 5/1994 |
| WO | 96/26693 A1 | 9/1996 |
| WO | 98/07397 A1 | 2/1998 |
| WO | 99/44552 A1 | 9/1999 |
| WO | 00/23016 A1 | 4/2000 |
| WO | 00/55542 A1 | 9/2000 |
| WO | 00/67685 A1 | 11/2000 |
| WO | 02/38091 A1 | 5/2002 |
| WO | 03/000079 A2 | 1/2003 |
| WO | 03/072008 A2 | 9/2003 |
| WO | 2005/007060 A2 | 1/2005 |
| WO | 2005/082301 A1 | 9/2005 |
| WO | 2006/110405 A2 | 10/2006 |
| WO | 2010/060931 A1 | 6/2010 |
| WO | 2011/019603 A1 | 2/2011 |

OTHER PUBLICATIONS

BioCompression Systems, Inc. (Moonachie, NJ); Product literature for Sequential Circulators; 15 pgs.; Oct. 1997.

Cothera LLC; VPULSE System Users Manual; 100149 Rev E; ©2013; 18 pgs. (manual rev. dated Jul. 2013).

Johns Hopkins Medicine; Patient guide to UCL injuries of the elbow (ulnar collateral ligament); 8 pages; Sep. 3, 2010; retrieved from the internet Apr. 20, 2015 (http:/www.hopkinsortho.org/ucl.html).

Van Eps et al.; distal limb cryotherapy for the prevention of acute laminitis; Clin Tech Equine Pract; vol. 3; pp. 64-70; Mar. 2004.

Van Eps et al.; Equine laminitis: cryotherapy reduces the severity of the acute lesion; Equine Veterinary Journal; vol. 36; No. 3; pp. 255-260; Apr. 2004.

Webster Dictionary; Shunt (definition); Merriam-Webster, Inc.; 11 pages; retrieved from the internet (https://www.merriam-webster.com/dictionary/shunt on Apr. 13, 2018.

* cited by examiner

INTEGRATED MULTISECTIONAL HEAT EXCHANGER

CROSS REFERENCE TO RELATED APPLICATIONS

This application is a continuation of U.S. patent application Ser. No. 14/819,276, filed Aug. 5, 2015, titled "INTEGRATED MULTISECTIONAL HEAT EXHANGER," now U.S. Patent Application Publication No. 2016/0038336, which claims priority to U.S. Provisional Patent Application No. 62/033,569, filed Aug. 5, 2014, and "INTEGRATED MULTISECTIONAL HEAT EXCHANGER," and U.S. Provisional Patent Application No. 62/057,091, filed Sep. 29, 2014, and titled "INTEGRATED MULTISECTIONAL HEAT EXCHANGER," each of which are herein incorporated by reference in their entireties for all purposes.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to therapy of an animate body, and more particularly a therapeutic wrap of the type having circulating fluid to provide cooling, heating, and/or compression to a human or animal body part.

BACKGROUND

It is now common to apply cold and compression to a traumatized area of a human body to facilitate healing and prevent unwanted consequences of the trauma. In fact, the acronym RICE (Rest, Ice, Compression and Elevation) is now used by many.

Typically thermally-controlled therapy involves cold packing with ice bags or the like to provide deep core cooling of a body part. Therapy often involves conventional therapy wraps with a fluid bladder for circulating a cooled heat exchange medium. Elastic wraps are often applied over the therapy wrap to provide compression.

More recently therapy wraps including a pair of compliant bladders to contain fluids have been disclosed. The therapy wrap typically has a compliant bladder for containing a circulating heat exchange liquid alone or in combination with a compressive bladder which overlays the compliant bladder for pressing the bladder against the body part to be subjected to heat exchange. In general, the body heat exchanging component(s) of such an apparatus include a pair of layers defining a flexible fluid bladder through which a liquid is circulated. The structure embodying both the liquid bladder and compressive bladder component is often referred to as a "wrap." The liquid fed to the wrap is maintained at a desired temperature by passing the liquid through a heat exchanging medium such as an ice bath or a refrigeration unit. One such system is disclosed, for example, in U.S. Pat. No. 6,178,562 to Elkins, the disclosure of which is herein incorporated for all purposes by reference.

Therapy wraps can be used to provide therapy in a variety of contexts whether for humans, equine animals, dogs, or any other mammal. Therapy wraps can be shaped and designed for application to a variety of anatomical body parts such as a hoof, a shoulder, a knee, a leg, a head, and more.

A problem occurs when applying the wrap to such complex shapes. Bending of the wrap in one or more directions can cause localized kinking or buckling in the bladder. In some cases, one or more fluid pathways becomes crimped or completely occluded, thereby inhibiting fluid flow and operation. This type of kinking generally occurs because of the inability of the material to conform to the complex shape of the anatomical part to which it is applied. It is believed that, in part, the material collapses and/or bunches when wrapped around tight radiuses.

There is the need for a wrap that is conformable to a complex anatomical shape and provides efficient heat transfer over the treatment surface under compressive force. There is a need for a wrap that reduces the risk of kinking or buckling. There is the need to provide a wrap that improves patient comfort.

There is the need for a therapeutic wrap that overcomes the above and other problems. There remains a need to provide improved temperature-controlled therapy apparatus and methods for their use.

SUMMARY OF THE DISCLOSURE

The present invention relates generally to therapy of an animate body, and more particularly a therapeutic wrap of the type having circulating fluid to provide cooling, heating, and/or compression to a human or animal body part.

In some embodiments, a multi-sectional therapy wrap is provided. The therapy wrap can include a first wrap section comprising a first fluid bladder, the first fluid bladder having a first interior fence that defines a first fluid flow path through the first fluid bladder; a second wrap section comprising a second fluid bladder, the second fluid bladder having a second interior fence that defines a second fluid flow path through the second fluid bladder, wherein the second wrap section overlaps at least a portion of the first wrap section; and a junction connecting the first fluid bladder of the first wrap section with the second fluid bladder of the second wrap sections, the junction partitioned into a first portion and a second portion with a third interior fence, wherein the third interior fence is aligned with both the first interior fence and the second interior fence to integrate the first fluid flow path with the second fluid flow path.

In some embodiments, the first wrap section comprises two sheets of material that are welded together to form the first fluid bladder, and the second wrap section comprises a third sheet welded to one of the two sheets that form the first fluid bladder.

In some embodiments, the therapy wrap further includes a manifold in fluid communication with the first wrap section, the manifold comprising a fluid inlet and a fluid outlet in fluid communication with the first fluid bladder.

In some embodiments, the first interior fence extends from the manifold to divide a portion of the first fluid bladder adjacent the manifold into a fluid outflow tract and a fluid inflow tract.

In some embodiments, the first fluid bladder comprises a first set of attachments points that are configured to limit expansion of the first fluid bladder and facilitate fluid flow through the first fluid bladder.

In some embodiments, the second fluid bladder comprises a second set of attachment points that are configured to limit the expansion of the second fluid bladder and facilitate fluid flow through the second fluid bladder.

In some embodiments, the attachment points of the second set have a larger diameter than the attachment points of the first set.

In some embodiments, the attachment points of the second set are spaced farther apart than the attachment points of the first set.

In some embodiments, the second wrap section comprises a curved biasing element adapted to bias the second wrap section against a patient's neck.

In some embodiments, the second wrap section comprises a pocket for removably receiving the curved biasing element.

In some embodiments, the first wrap section comprises one or more stiffening elements adapted to maintain the shape of the first wrap section against compression.

In some embodiments, the therapy wrap further includes a spacer disposed between the first wrap section and the second wrap section and adjacent the junction.

In some embodiments, the therapy wrap further includes one or more shunts disposed within the junction, wherein the one or more shunts are configured to prevent or reduce the likelihood of kinking in the junction.

In some embodiments, a clasp for securing a therapy wrap to a patient's neck is provided. The clasp can include a first curved arm; a second curved arm; and a hinge that rotatably connects the first curved arm with the second curved arm such that that the first curved arm and the second curved arm have an open configuration adapted to receive the patient's neck and a closed configuration adapted to partially surround the patient's neck such that there is a gap between the first curved arm and the second curved arm.

In some embodiments, the hinge comprises a torsion spring that biases the first curved arm and the second curved arm into the closed configuration.

In some embodiments, the clasp further includes a first support extending from a backside of the first curved arm and a second support extending from a backside of the second curved arm, wherein the first support and the second support are adapted to support the patient's neck in a prone position.

In some embodiments, the first support and the second support are wedge shaped.

In some embodiments, a multi-sectional therapy wrap is provided. The therapy wrap can include a first wrap section comprising a first fluid bladder and a gas bladder, the first fluid bladder having a first interior fence that defines a first fluid flow path through the first fluid bladder; a second wrap section comprising a second fluid bladder, the second fluid bladder having a second interior fence that defines a second fluid flow path through the second fluid bladder, wherein the second wrap section overlaps at least a portion of the first wrap section; and a junction connecting the first fluid bladder of the first wrap section with the second fluid bladder of the second wrap sections, the junction partitioned into a first portion and a second portion with a third interior fence, wherein the third interior fence is aligned with both the first interior fence and the second interior fence to integrate the first fluid flow path with the second fluid flow path.

In some embodiments, the first wrap section comprises three sheets of material that are welded together to form the first fluid bladder and the second fluid bladder, and the second wrap section comprises a fourth sheet welded to one of the three sheets that form the first fluid bladder.

In some embodiments, the therapy wrap further includes a manifold in fluid communication with the first wrap section, the manifold comprising a fluid inlet and a fluid outlet in fluid communication with the first fluid bladder, and a gas line in communication with the gas bladder.

In some embodiments, a multi-sectional therapy wrap is provided. The therapy wrap can include a first wrap section comprising a first fluid bladder, the first fluid bladder having a first interior fence that defines a first fluid flow path through the first fluid bladder, the first fluid bladder having a fluid connector comprising a first port and a second port, wherein the first interior fence divides the fluid connector and separates the first port from the second port; and a second wrap section comprising a second fluid bladder, the second fluid bladder having a second interior fence that defines a second fluid flow path through the second fluid bladder, the second fluid bladder having a receptacle comprising a third port and a fourth port, wherein the second interior fence divides the receptacle and separates the third port and the fourth port; wherein the fluid connector is fluidically coupled to the receptacle to allow fluid to flow between the first wrap section and the second wrap section.

In some embodiments, the fluid connector is reversibly coupled to the receptacle.

In some embodiments, the fluid connector is permanently coupled to the receptacle.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Therapy wraps can be used to treat patients by providing cooling or heating of various body parts. The therapy wrap typically includes a heat exchanger portion for circulating a heat exchange fluid, and can additionally include a compression portion to provide compression to the area being treated and to improve contact between the therapy wrap and the body part, which improves heat transfer. The heat exchanger portion can be a fluid bladder or chamber, while the compression portion can be a gas bladder or chamber. To use the therapy wrap, the heat exchanger portion (fluid bladder) is typically placed against or adjacent the patient's skin while the compression portion (gas bladder) is located on the outside such that the heat exchanger portion is between the compression portion and the patient's body. The fluid bladder of the therapy wrap is typically connected to a fluid reservoir and the gas bladder is typically connected to an air pump. Flexible tubing can be used to provide the connections to the therapy wrap.

For body parts with a relatively simply geometry, such as a limb, the therapy wrap may be wrapped around the limb with relative ease. For example, a generally rectangular therapy wrap may be adequately wrapped around an arm or a leg in many cases. However, other portions of the body, such as the shoulder and neck region, have more complex geometry that may require the use of multiple therapy wraps and/or therapy wraps with a more complex geometry.

Although multiple therapy wraps can be used to provide coverage of a body region with a complex geometry, the use of multiple therapy wraps may require the use of multiple fluid reservoirs and/or multiple sets of tubing and connections, which can increase the cost, the complexity of the set up, and the clutter around the patient.

A multi-sectional therapy wrap with a relatively complex geometry can be used to solve these problems. For example, FIGS. 1A-1G illustrate an embodiment of a multi-sectional therapy wrap 100 that includes a first wrap section 102 and a second wrap section 104 that can be used to cover the upper torso, the shoulders and the neck. The first wrap section 102 can be wrapped around the upper torso and shoulders, while the second wrap section 104 can be wrapped around the neck.

Figure 1A:
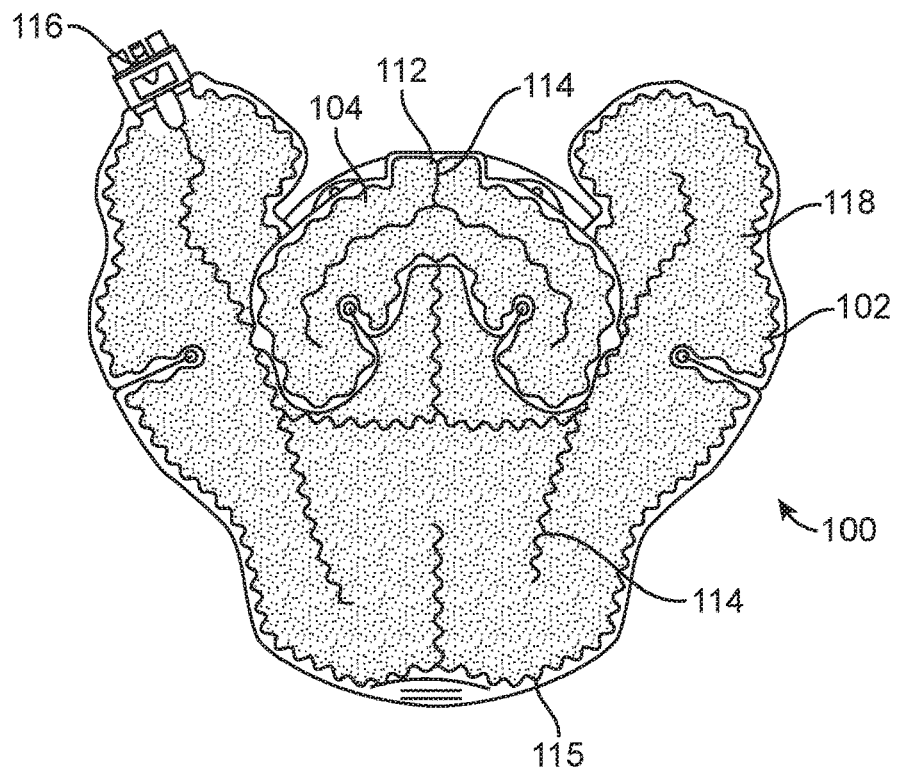
FIG. 1A is a view of the fluid side of one embodiment of a multi-sectional therapy wrap.
Figure 1B:
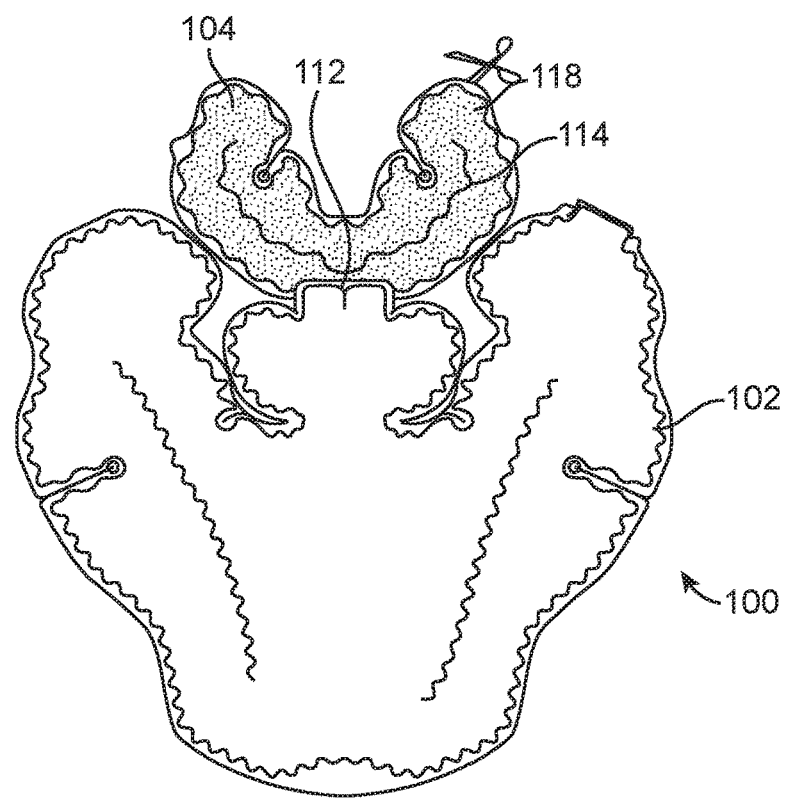
FIG. 1B is a view of predominantly the gas side of the multi-sectional therapy wrap of FIG. 1A.
Figure 1C:
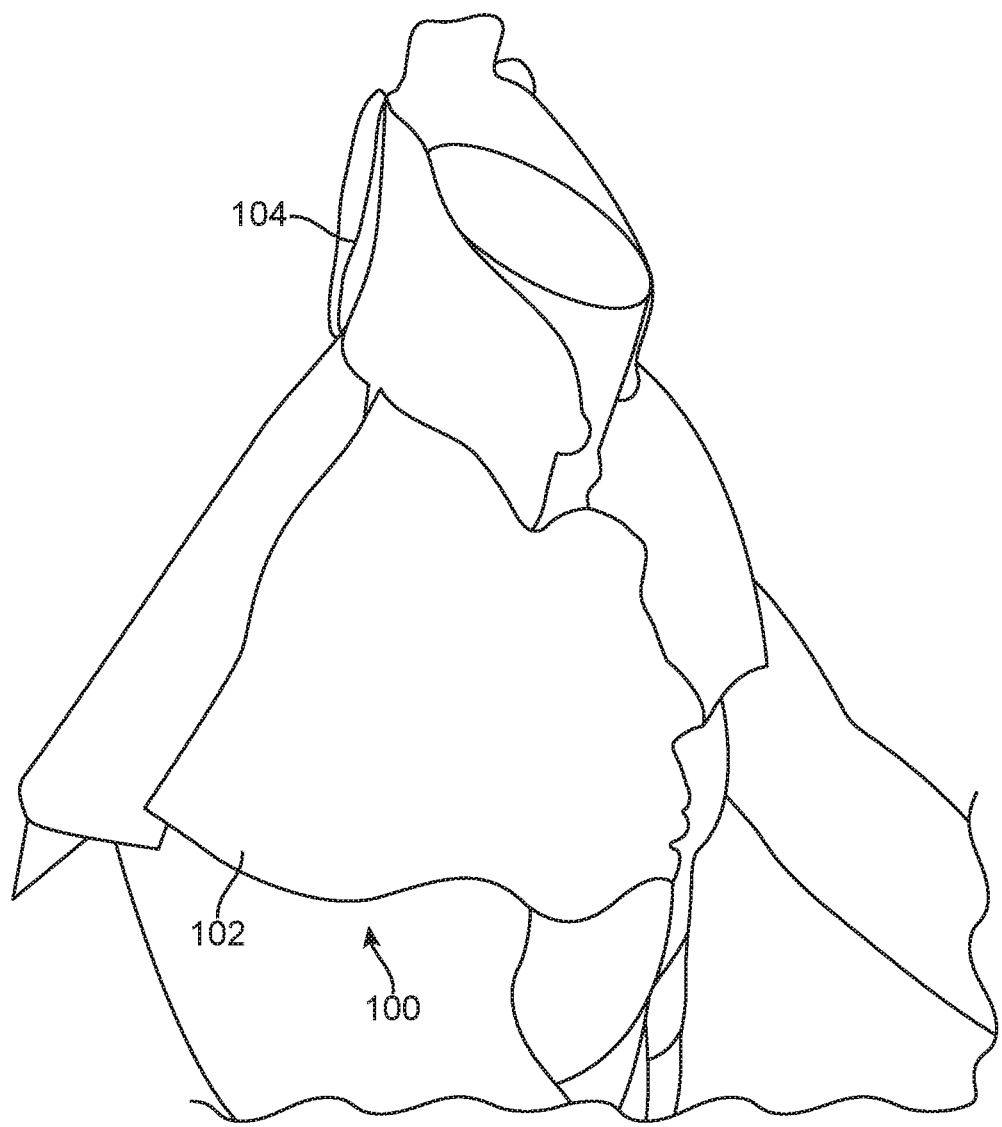
FIG. 1C is a side perspective view of the multi-sectional therapy wrap of FIG. 1A as worn.
Figure 1D:
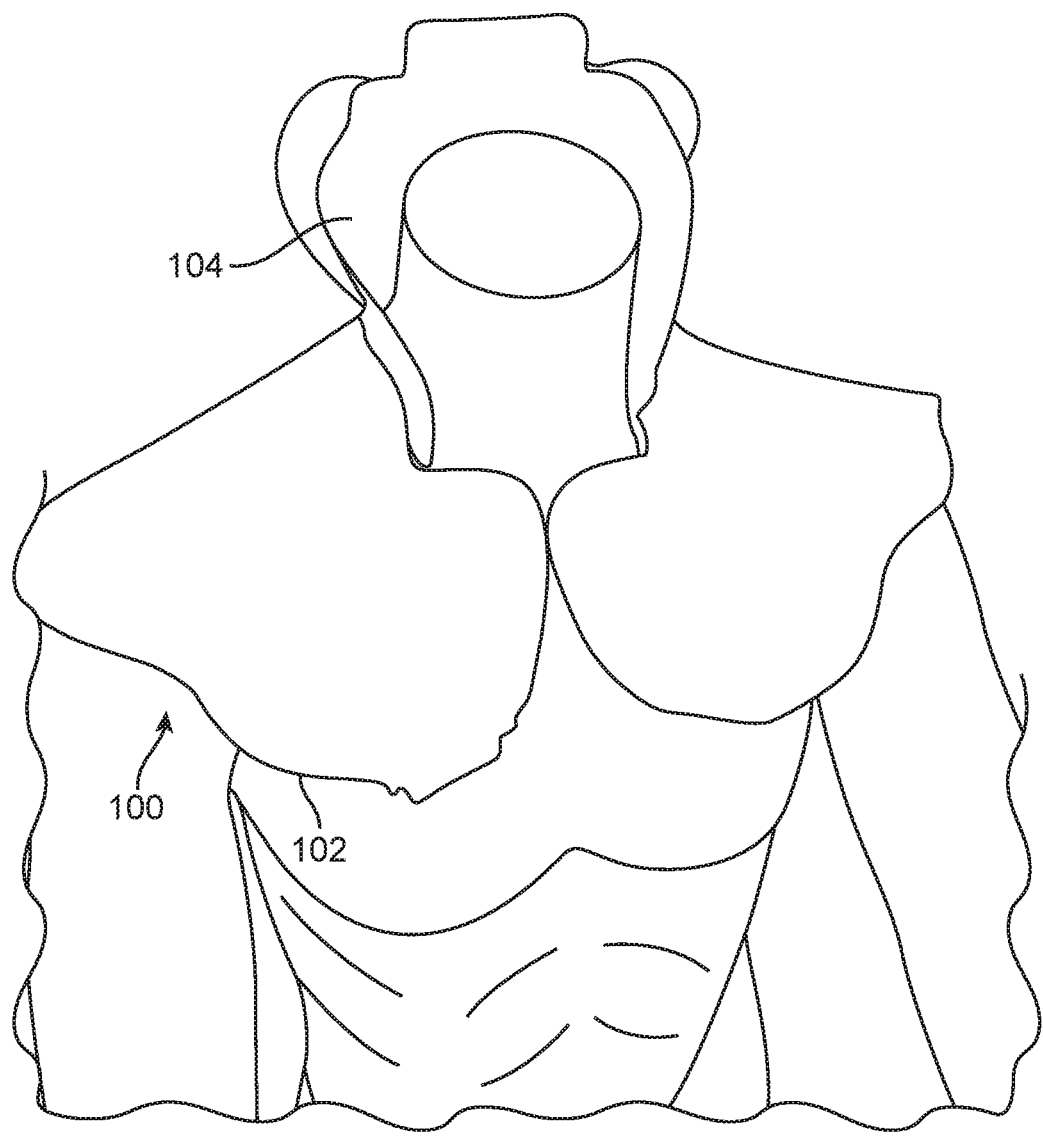
FIG. 1D is a front perspective view of the multi-sectional therapy wrap of FIG. 1A as worn.
Figure 1E:
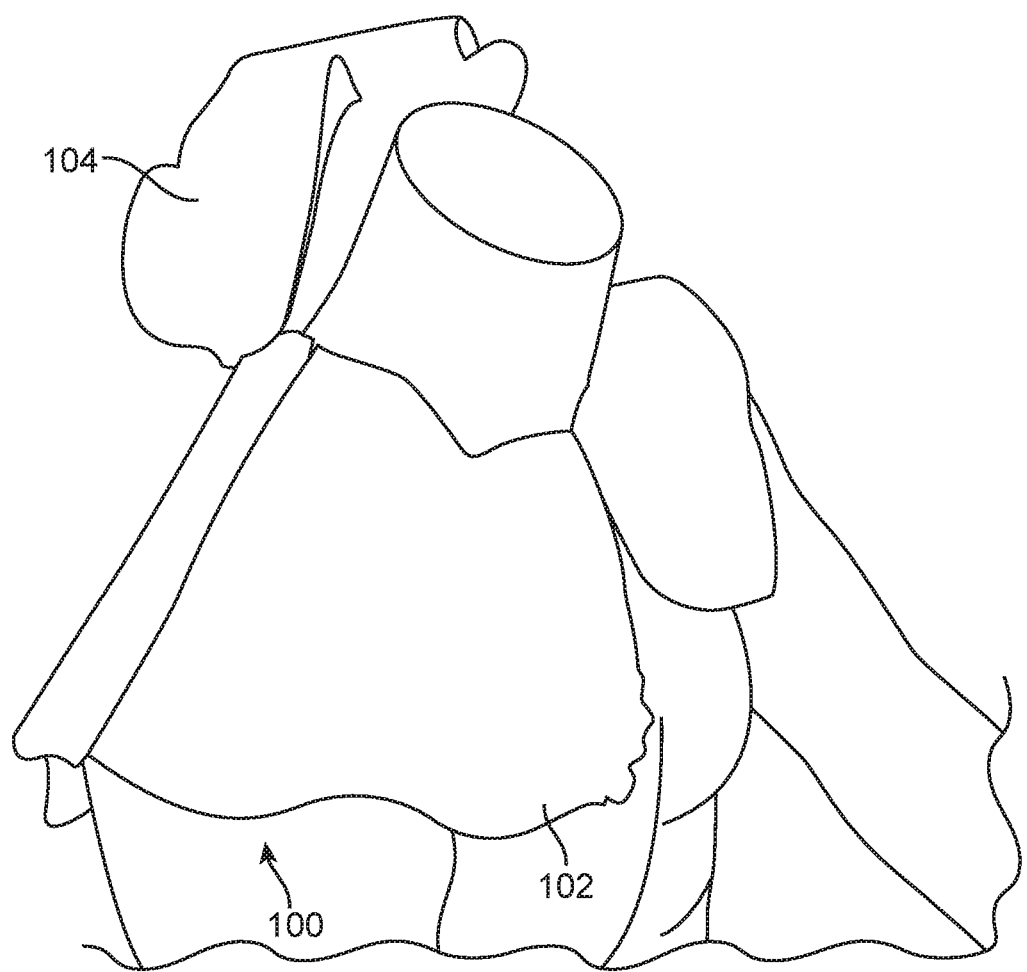
FIG. 1E is another side perspective view of the multi-sectional therapy wrap of FIG. 1A as partially worn.
Figure 1F:
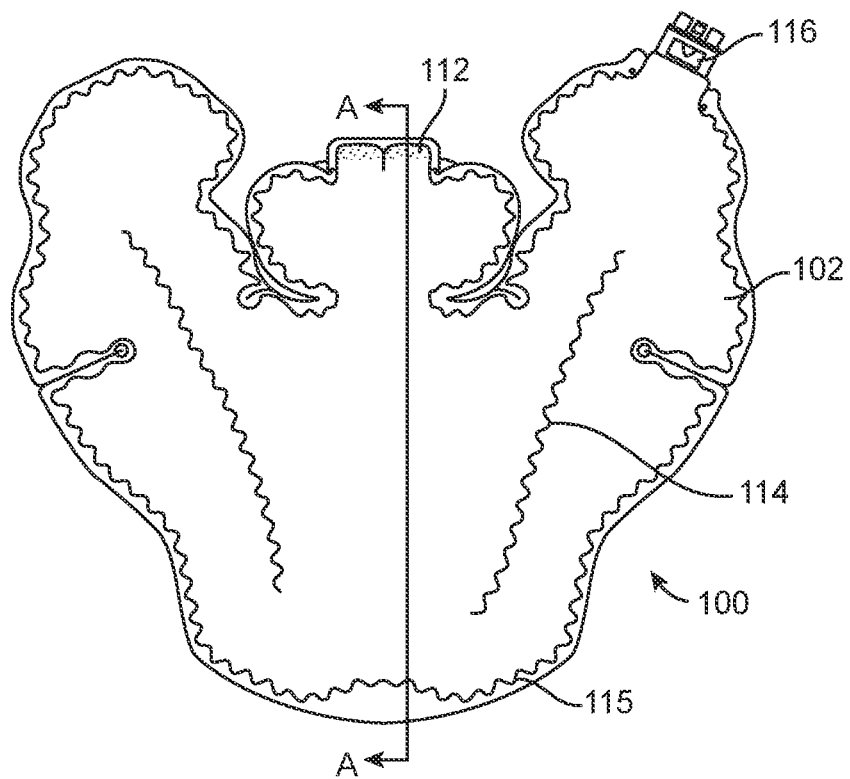
FIG. 1F is a view of the gas side of one embodiment of a multi-sectional therapy wrap that includes a sectional line A-A.
Figure 1G:
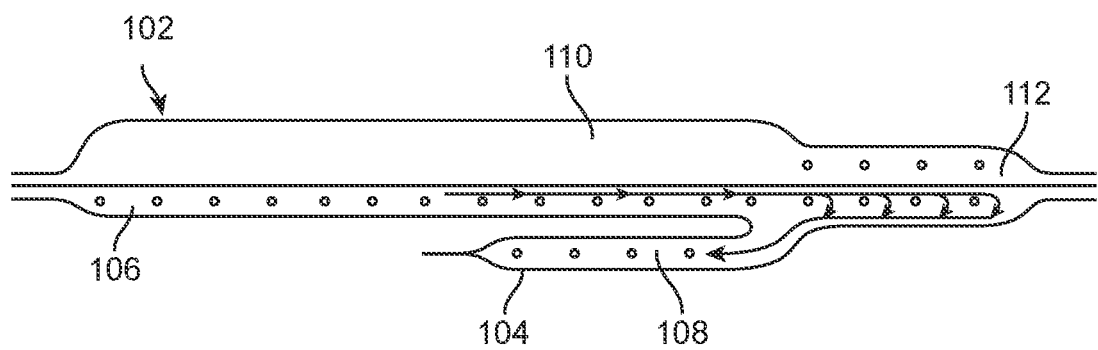
FIG. 1G is a cross-sectional view of the multi-sectional therapy wrap of FIG. 1F taken along section line A-A.

Both the first wrap section 102 and the second wrap section 104 can include a fluid bladder 106, 108 that functions as a heat exchanger. Because providing compression around the neck can be uncomfortable, in some embodiments, as shown in FIGS. 1A-1G, the first wrap section 102 that wraps around the upper torso and the shoulders can include an air bladder 110 for providing compression, while the second wrap section 104 can be free of the air bladder and include only the fluid bladder 108, as illustrated in FIG. 1G. Instead of compression from an air bladder, the second wrap section 104 can be maintained in contact with the patient's skin through other devices, such as a clasp, straps, stays, biased inserts, and/or other means, as will be described in further detail below.

The first therapy wrap section 102 and the second therapy wrap section 104 can be joined together such that the fluid bladder 106 of the first therapy wrap section 102 is in fluid communication with the fluid bladder 108 of the second therapy wrap section 104. As shown, the two therapy wrap sections can be joined together via an overlapping section between the two fluid bladders that forms a fluid box, chamber or junction 112, as shown in FIGS. 1A, 1B and 1G. The fluid junction 112 between the two fluid bladders allows the heat transfer fluid to pass from one fluid bladder to the other fluid bladder.

The specialized junction 112 between the two wrap sections provides a way to create a wrap with a complex geometry and configuration, such as a wrap with two overlapping wrap sections, each with a fluid bladder on the skin facing side of the wrap section. The junction 112 provides a transition between the two wrap sections that is kink resistant, allows fluid flow between the two wrap sections, and accommodates virtually any geometry for the two wrap sections, where each wrap section can be made by layering together two or three sheets of material together to form the bladder(s), as described in more detail below. These advantages cannot be all replicated by simply folding one portion of a wrap over another portion of the wrap. For example, the folding method tends to create a kink or a kink prone region at the fold, and would also have limited geometry for a wrap formed from a plurality of sheets. In contrast, the junction 112 can provide a 180 degree bend in the fluid flow path without creating a kink or fold between the wrap sections. In addition, the use of the junction 112 allows different types of wrap sections to be joined, with one wrap section having both a fluid bladder and a gas bladder, while the second wrap section may be a fluid bladder.

A single manifold 116 with a fluid intake line, a fluid outlet line, and an optional gas line can be used to operate the multi-sectional therapy wrap. For example, as shown, the manifold 116 can be attached to and integrated with one of the therapy wrap sections, such as the first wrap section 102 as shown. Fluid enters the fluid bladder of the first wrap section through the fluid intake line. The fluid can be directed through the first fluid bladder until it reaches the fluid junction 112. The fluid passes through the fluid junction 112 from the first fluid bladder to the second fluid bladder. Interior fluid guides or fences 114 in both fluid bladders can guide the fluid flow along a predetermined flow path within each fluid bladder and from one fluid bladder to the other fluid bladder. Once in the second fluid bladder, the heat transfer fluid flows through the second fluid bladder and returns to the fluid junction 112 to flow back into the first fluid bladder. An interior fluid guide or fence 114 can be used to separate the fluid junction 112 into inlet and outlet portions. The fluid then flows through the remaining portion of the first fluid bladder until it reaches the fluid outlet in the manifold 116.

In addition, the flow path may be divided into a plurality of fluidic channels by a series of attachment points. The attachment points connect opposite walls of the bladder in a thickness direction. The exemplary attachment points, generally designated 118, may be formed by spot welding. In various respects, the attachment points are referred to informally as "dots." The dots may be performed with conventional techniques such as RF or heat welding. The exemplary dots are circular based on the nature of the welding process, but one will appreciate that the dots may have different shapes. "Attachment point" is to be understood as used in the art and generally refers to points that are essentially one-dimensional as opposed to lines, shapes, and other similar features. The dots are similar in many respects to fences except that they are single points rather than a shape or line.

In some embodiments, the therapy wrap may also be constructed with a gas bladder 110. The gas bladder 110 can also have interior fences 114 to help control or limit the expansion of the air bladder as it is filled with gas. Further description of general therapy wrap features and construction techniques can be found in U.S. Pat. No. 6,695,872, which is herein incorporated by reference in its entirety for all purposes. In addition, both wrap sections can have a peripheral fence 115 that extends around the perimeter of the wrap sections. The peripheral fence 115 can be used to join the plurality of sheets together and form a fluid or gas tight seal around the periphery of the wrap.

Figure 1J:
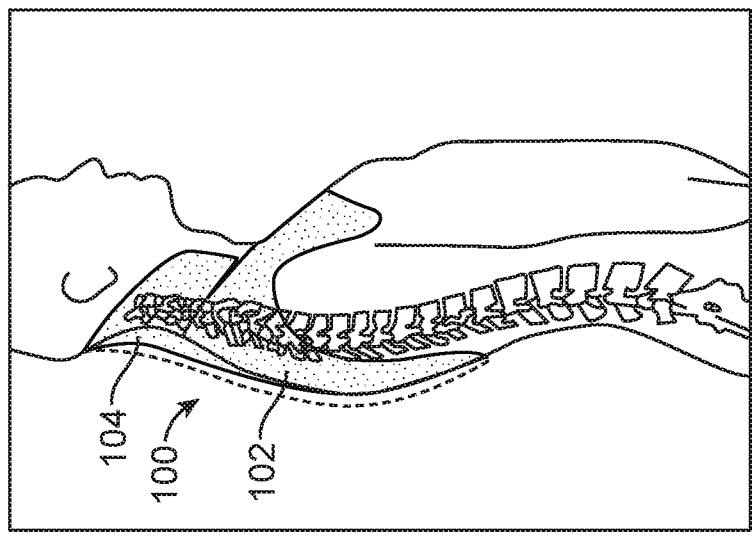
FIGS. 1H-1J illustrate various views of an embodiment of a multi-sectional therapy wrap covering the upper back and neck.
Figure 1I:
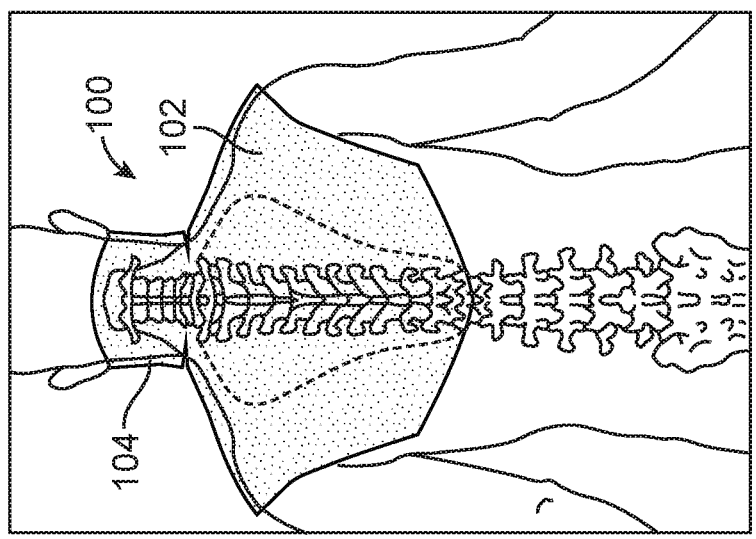
Figure 1H:
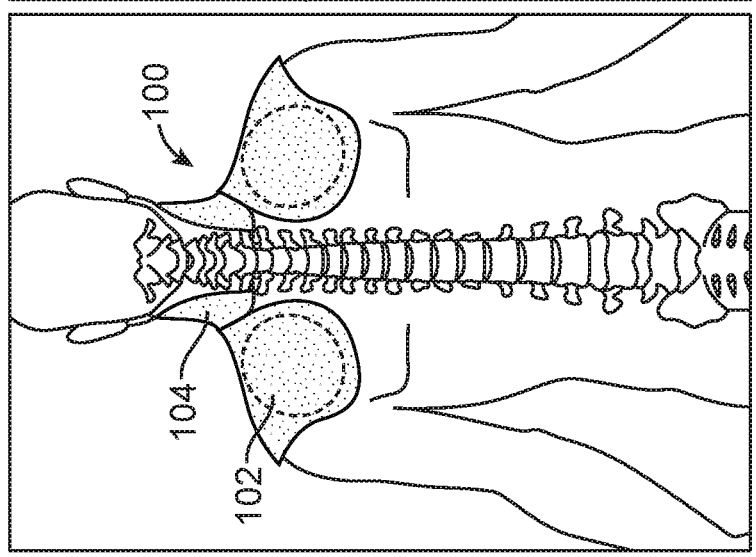

As shown in FIGS. 1H-1J, the therapy wrap 100 can be used to provide thermal therapy, such as cooling, to the thoracic and cervical portion of the spine. The first wrap section 102 can cover the upper back and thoracic spine, while the second wrap section 104 can cover the cervical spine and portions of the neck including neck muscles. In some embodiments, the first wrap section can extend further to also cover one or more of the lumbar spine and the sacral spine.

Figure 2A:
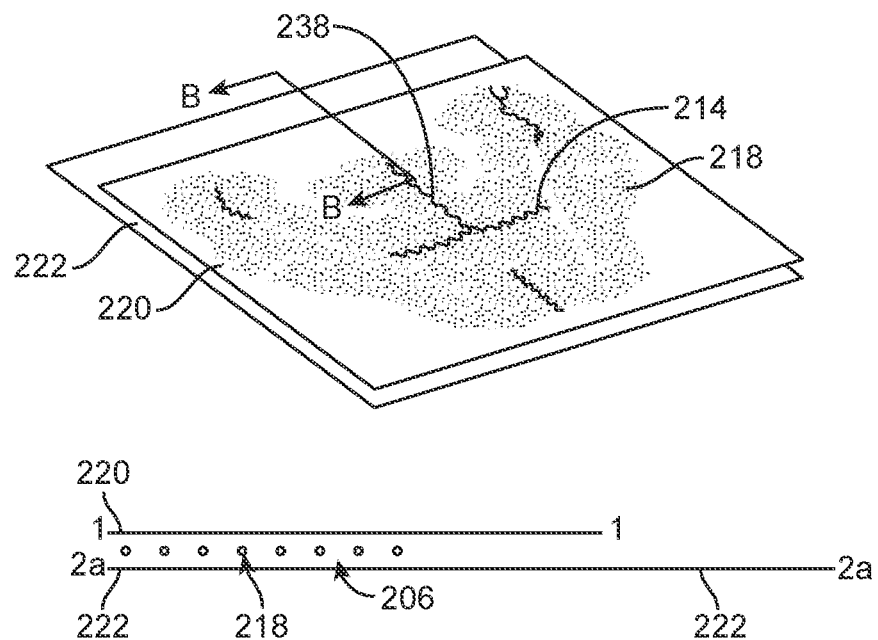
FIGS. 2A-2I illustrate the assembly of a multi-sectional therapy wrap.

FIGS. 2A-2H illustrate one embodiment of a method of manufacturing a multi-sectional therapy wrap 200 with a junction 212 to join the first wrap section 202 with the second wrap section 204. The multi-sectional therapy wrap 200 can be manufactured from a plurality of sheets of material, such as a polymer sheets or fabrics, that can be welded together using, for example, RF energy or heat. FIG. 2A illustrates the construction of the fluid bladder 206 for the first wrap section 202. A first sheet 220 can be aligned over a second sheet 222, by for example, aligning the bottom edges of the sheets together. In some embodiments, the second sheet 222 can be larger in one dimension than the first sheet 220. In other embodiments, the second sheet 222 can be larger in two dimensions. In some embodiments, alignment can be done with one edge, a plurality of edges, and/or the use of one or more additional alignment features. The second sheet 222 can be larger than the first sheet 220 to accommodate a third overlapping sheet that is used to form the second wrap section. A pattern of attachments points 218, or microdots, can be generated by spot welding the two sheets together. Some interior fences 214 can also be welded at this time to provide fences 214 for the fluid bladder that are not necessarily shared with the gas bladder. The first sheet 220 can have a template of the microdot pattern and fence positioning marked on the sheet to guide the welding process.

Figure 2B:
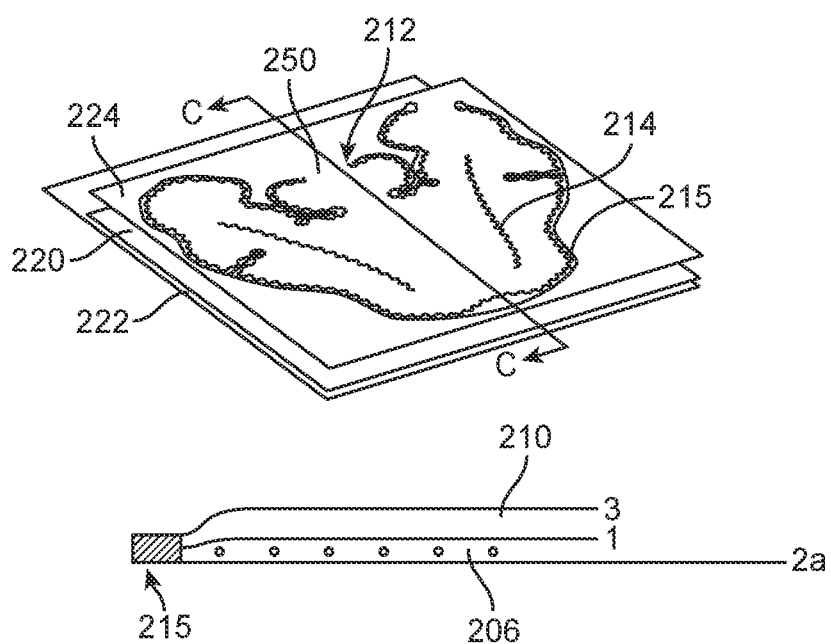

FIG. 2B illustrates the addition of the third sheet 224, which can be placed over the first sheet 220 to form the gas bladder 210. The third sheet 224 can include interior fences 214 that can extend through both the gas bladder 210 and the fluid bladder 206. In addition, the third sheet 224 can include an exterior fence 215 around the perimeter of the wrap section that can extend through both the gas bladder and the fluid bladder. The third sheet 224 can also include a template for the fences to guide the welding process. The perimeter fence 215 can have a gap 250 for the junction 212 that allows fluid to pass through from the first wrap section 202 to the second wrap section 204.

Figure 2C:
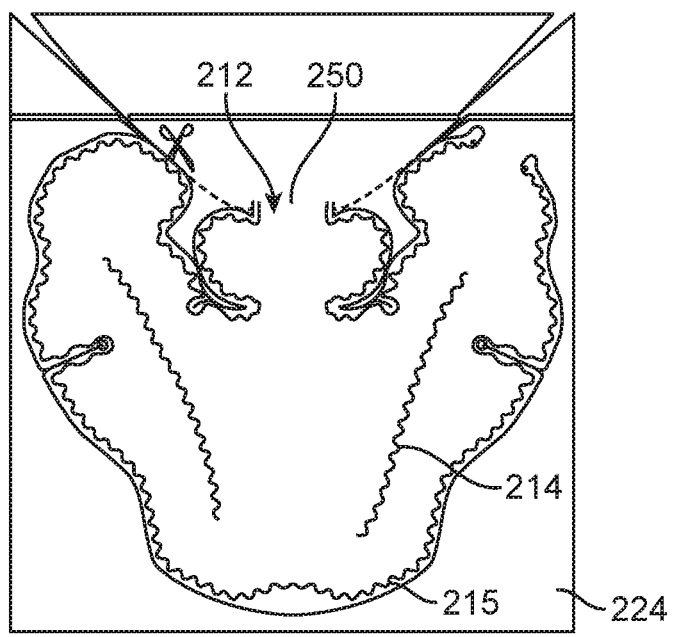

FIG. 2C illustrates the formation of the junction 212. The third sheet 224 can have a template to guide cuts through the sheets to the edges of the junction 212. In some embodiments, the cutting template can also extend through the first sheet 220. The template to guide the cuts can be formed by creating a line of dots through welding or otherwise marking the sheets. These dot lines can be formed when forming the attachment points 218 or dots for the fluid bladder, or the dot lines can be formed separately. The cuts can be made to skirt along the edges of the first wrap section 202. In this embodiment, the junction 212 is positioned at the neck section of the wrap, but in other embodiments, any section of the wrap can have one or more junctions or no junction at all.

Figure 2D:
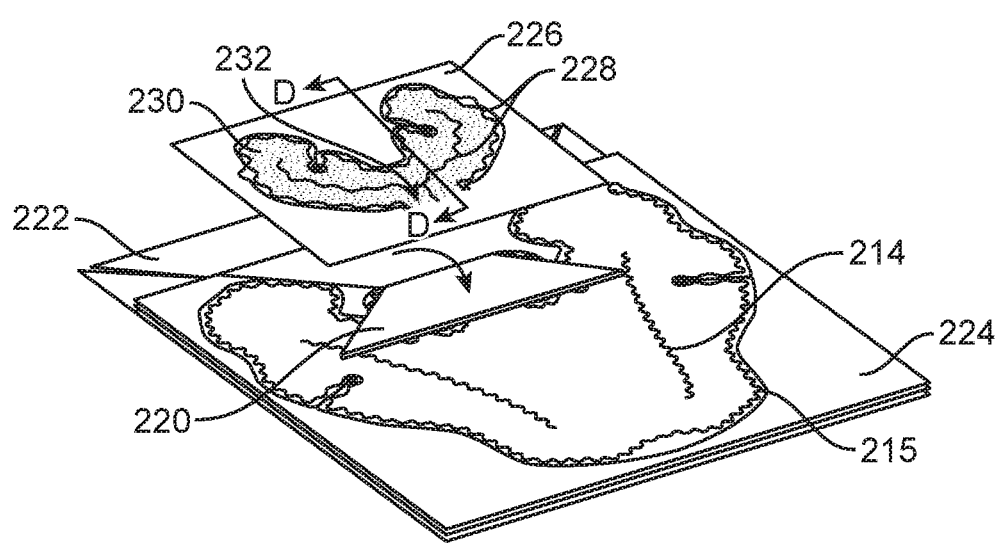
Figure 2E:
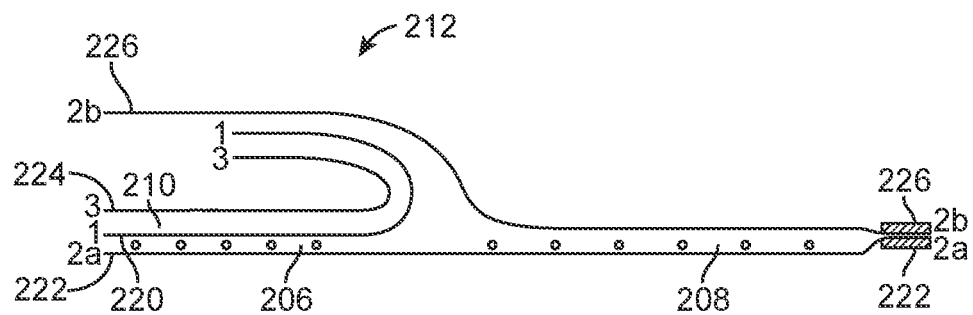

FIG. 2D illustrates the continued formation of the junction 212 along with the addition of the second wrap section 204. To form the second wrap section 204, the cut portion of the first sheet 220 and the third sheet 224 can be folded over against the third sheet 224 of the gas bladder to expose an underlying portion of the second sheet 222. A fourth sheet 226 can be placed over the exposed, underlying portion of the second sheet 222 by aligning, for example, one edge of the fourth sheet 226 with one edge of the second sheet 222, or by the use of additional or alternative alignment features. The fourth sheet 226 can then be welded or otherwise attached to the second sheet 222, by for example, forming perimeter and interior fences 228 and attachment points 230. The attachment points 230 in the second wrap section 204 can have a different spacing with a different dot or weld size than the attachment points 218 in the first wrap section 202, especially when the second wrap section 204 is to be used as a neck wrap. In some embodiments, the spacing and dot size can be the same as other wrap sections. In other embodiments, the spacing and dot size can be larger or smaller than in other wrap sections. The perimeter fence 228 of the second wrap section 204 can also have a gap 232 that matches the gap 250 in the perimeter fence 214 of the first wrap section 202. In some embodiments, the two gaps can be aligned together to form a portion of the junction 212. The width of the gaps defines the width of the channel or flow path through the junction 212. In some embodiments, at this stage, care should be taken to avoid welding the folded portion of the first sheet 220 and the third sheet 224. As shown in FIG. 2E, which illustrates a cross-section of the second wrap section 204 taken along the sectional line D-D in FIG. 2D, the fourth sheet 226 and the second sheet 222 form a second wrap section 204 that includes a single fluid bladder 208 without any gas bladder, an unfinished junction 212, and the gas bladder 210 and fluid bladder 206 of the first wrap section 202.

Figure 2F:
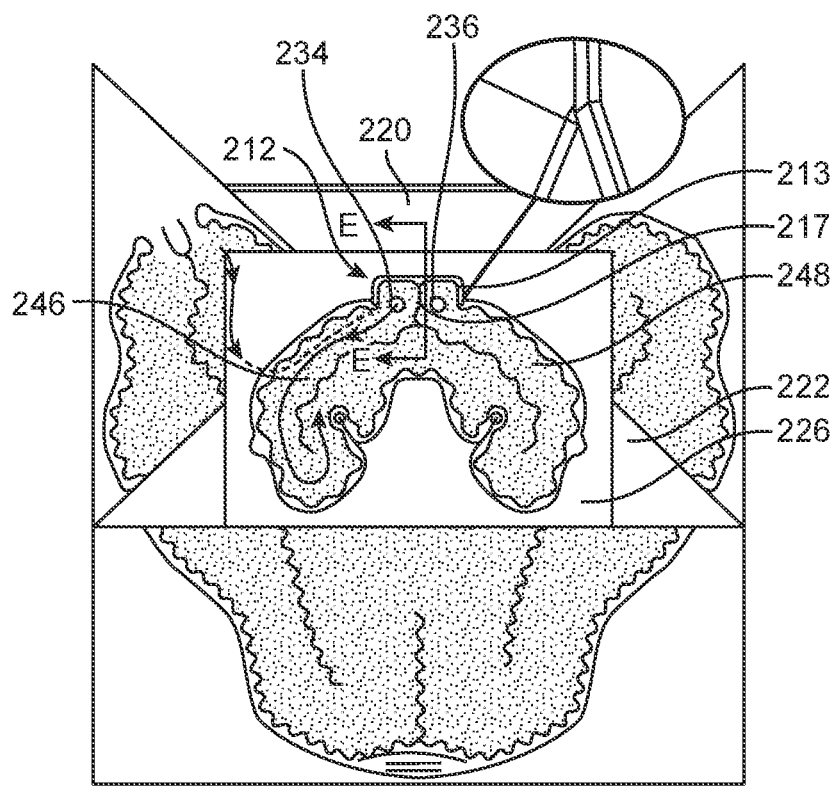
Figure 2F:
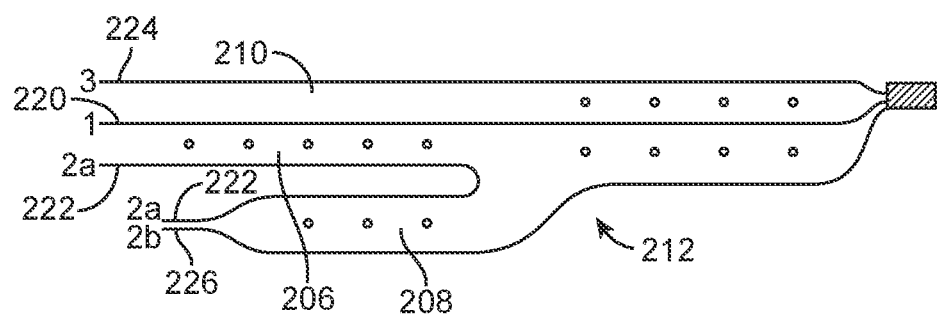
Figure 2G:
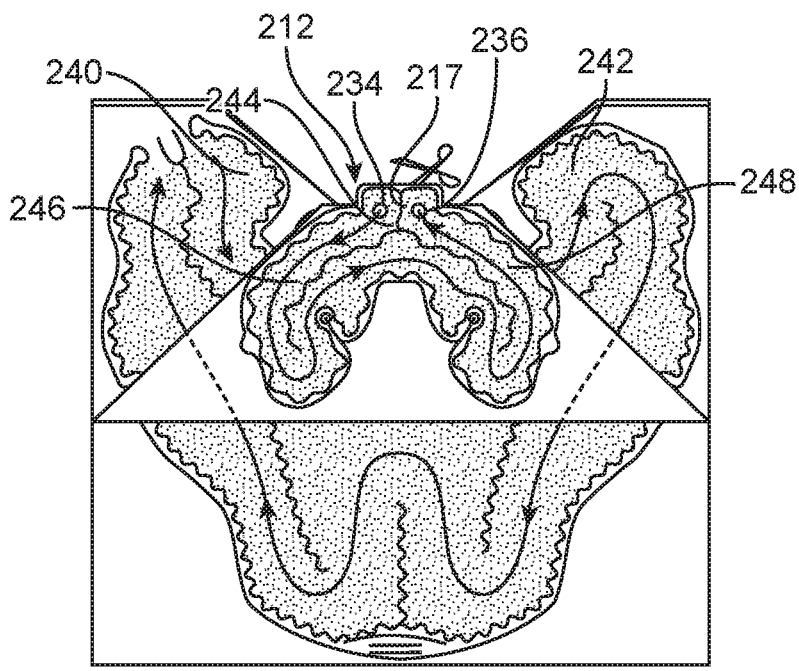

FIGS. 2F and 2G illustrate the completion of the junction 212. The cutout portion of the second sheet 222 with the fourth sheet 226 can be folder over against the second sheet 222 of the fluid bladder 206 of the first wrap section 202. The previously folded portion of the first sheet 220 and the third sheet 224 can be unfolded so that a portion of the fourth sheet 226 with the gap 232 overlaps with the cutout portion of the first sheet 220 with the gap 250. The overlapping portions of the first sheet 222 and the forth sheet 226 adjacent the gaps can be welded together to form the junction 212 between the two wrap sections. The junction 212 can have a perimeter fence 213 which connects the perimeter fences of the first wrap section 202 and the second wrap section 204. The junction 212 can also have an interior fence 217 that that divides the junction into a first section 234 that receives fluid from the first wrap section 202 and passes fluid to the second wrap section 204, and a second section 236 that receives fluid from the second wrap section 204 and passes fluid back to the first wrap section 202. In interior fence 217 of the junction 212 can also prevent or reduce kinking in the junction 212.

The portion of the first wrap section 202 adjacent the junction 212 can also have an interior fence 238, shown in FIG. 2A, that divides the first wrap section 202 into an outflow section 240 with respect to the junction 212 and an inflow section 242 with respect to the junction 212. Similarly, the portion of the second wrap section 204 adjacent the junction 212 can have an interior fence 244 that divides the second wrap section 204 into an inflow section 246 with respect to the junction 212 and an outflow section 248 with respect to the junction 212. The interior fences 217, 238, 244 of the junction 212 and the portions of the wrap sections adjacent the junction 212 can all be aligned to provide a flow path from the manifold to the first wrap section 202, from the first wrap section 202 to the junction 212, from the junction 212 to the second wrap section 204, through the second wrap section 204, back to the junction 212, and then back to the first wrap section 202, where the flow path continues through the rest of the first wrap section 202 and back to the manifold.

Figure 2H:
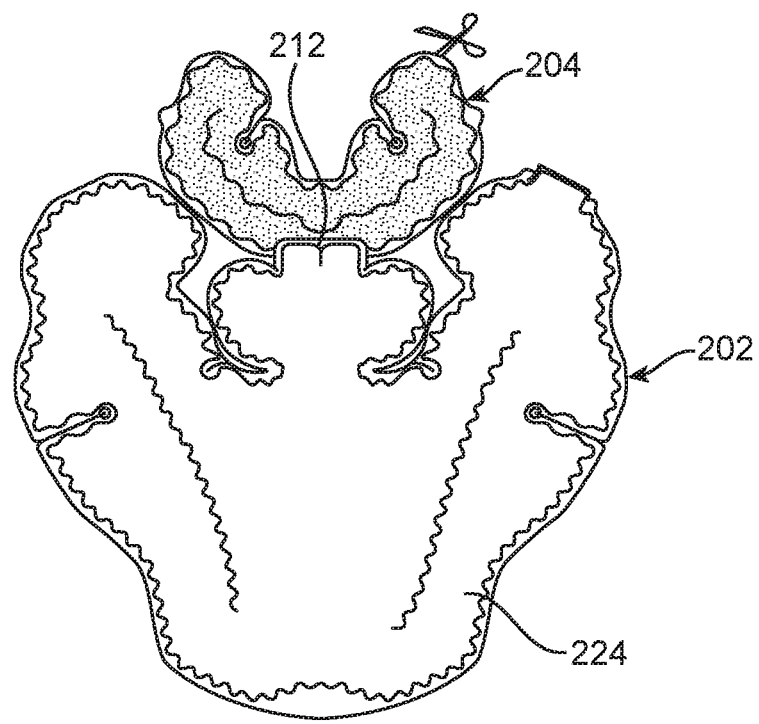
Figure 2I:
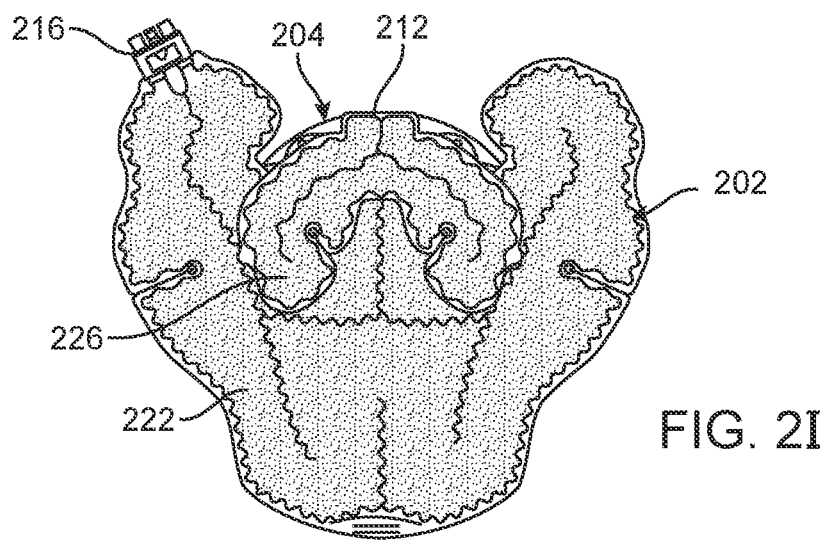

As shown in FIGS. 2G-2I, after the junction 212 is formed, the excess sheeting can be cut from the wrap sections 202, 204 and junction 212, and the manifold 216 can be attached to the first wrap section 202, although in other embodiments the manifold 216 can be attached to any of the wrap sections. As illustrated in FIG. 2I, the fluid bladder side of both wrap sections face the same direction and can be pressed against the patient's skin. In the illustrated embodiments, the second wrap section 204 can be wrapped around the patient's neck while the first wrap section 202 can be wrapped around the patient's shoulders and upper back. In some embodiments, the fluid sides of the wrap sections that are configured to be placed adjacent to skin can have indicators to help the patient or health care provider place and orient the wrap on the patient. The indicators can be a separate coloring, pattern, or marking that allows the user to distinguish the fluid side from the gas side of the wrap.

Straps with fasteners, such as a hook and loop type fastener, can be used to secure the first wrap section to the patient's shoulders and upper back. Inflation of the gas bladder of the first wrap section can provide further compression of the first wrap section 202 against the patient's skin. Although a strap with fasteners can be used to secure the second wrap section 204 to the patient's neck, use of a strap may constrict the patient's airway and be uncomfortable.

Figure 3A:
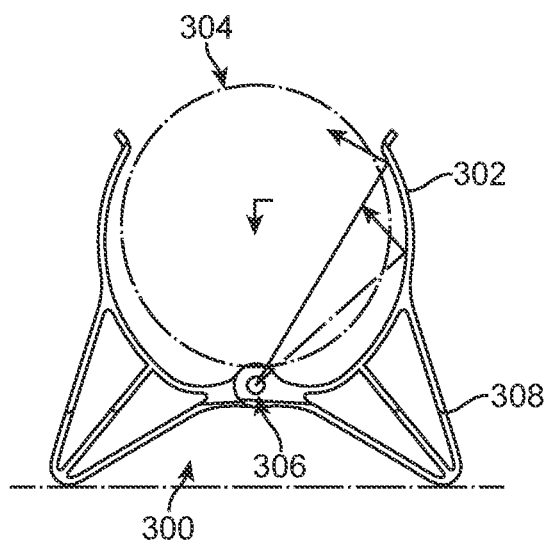
FIGS. 3A and 3B illustrate an embodiment of a pressure application device for improving contact between the patient's skin and the therapy wrap.
Figure 3B:
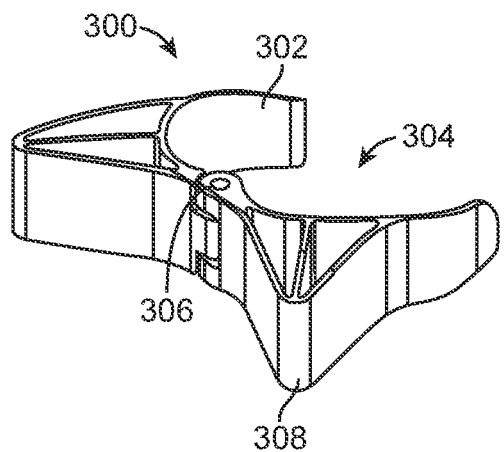

To avoid or prevent constriction of the patient's airway, other devices can be used to provide compression and/or to press the second wrap section 204 to the patient's skin. For example, FIGS. 3A and 3B illustrate a clasp 300 that can be used to secure the second wrap section to a portion of the patient's neck without fully encircling the patient's neck. When fully closed in a closed configuration, the clasp 300 retains an opening 304 between the ends of the two clasp arms 302. In some embodiments, the clasp 300 can encircle between about 50% to 90% of the patient's neck, or about 60% to 80%. The arms 302 can have a curved, interior surface that matches the contour of the body part to be secured, such as a portion of the patient's neck. The arms 302 can be rotatably attached together using a pivot 306 or hinge, which may be biased to the closed configuration by, for example, a torsion spring. Alternatively, the arms 302 can be closed by the application of a downward force provided by the patient's neck when the patient lies down. The pivot 306 can have a stop that prevents the arms 302 from fully closing. The spring or other biasing mechanism can be designed to apply a predetermined maximum level of force or pressure to the therapy wrap, or can provide an adjustable torsional force. The back of the arms 302 can have supports 308 that extend outwards from the arms 302 that can form a stable platform for supporting the clasp 300 and the patient's neck when the clasp 300 is in the closed configuration around the patient's neck and the patient is lying down on his or her back. The supports 308 can also be used to open the clasp 300 by grasping and squeezing the supports 308 together to open the arms 302 from the closed configuration to an open configuration that allows the clasp 300 to be removed from the patient's neck. The supports 308 can be wedge shaped with a rounded apex. The clasp 300 can be manufactured in several different sizes to accommodate necks of various sizes, or alternatively, the arms 302 of the clasp can be adjustable in length or circumference to cover a variety of neck sizes.

Figure 4A:
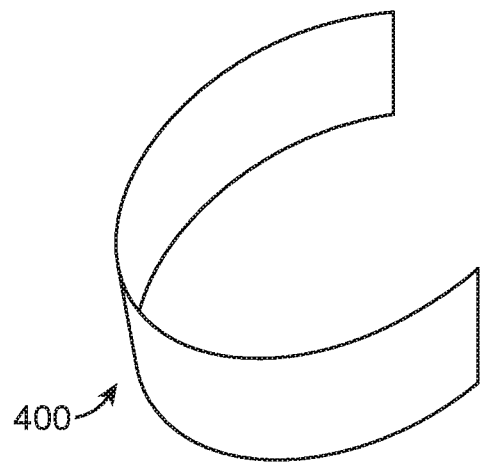
FIGS. 4A and 4B illustrate embodiments of therapy wrap inserts for shaping the therapy wrap.
Figure 4B:
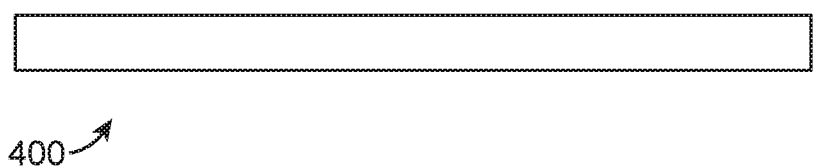

Other devices can also be used to secure the wrap around the patient's neck or other body part. For example, as illustrated in FIGS. 4A and 4B the therapy wrap or a sleeve for holding the therapy wrap can have pockets to receive inserts 400, which may be straight or curved and elastic or inelastic, or combinations of the above, depending on the application. Insertion of the inserts 400 into the pockets allows the wrap sections to be shaped and stiffened along predetermined forms and to bias the wrap sections towards the patient's skin. For example, insertion of a flat, curved C-shaped or collar-like insert 400, as illustrated in FIG. 4A, into the second wrap section can bias the second wrap section into a C-shape for securement around the neck, and the insert 400 can be flexible to limit the pressure or force exerted onto the neck. In addition, insertion of relatively straight inserts 400, as illustrated in FIG. 4B, or inserts 400 with a curvature matching the curvature of the spine or back of the patient into pockets in the first wrap section can be used to maintain the shape prevent the first wrap section from scrunching up from forces exerted by the straps while the wrap is being worn by the patient. These inserts 400 can be elongate strips or can be wider plates or sheets or material. In some embodiments, the inserts 400 can be made of a plastic or metal.

Figure 5A:
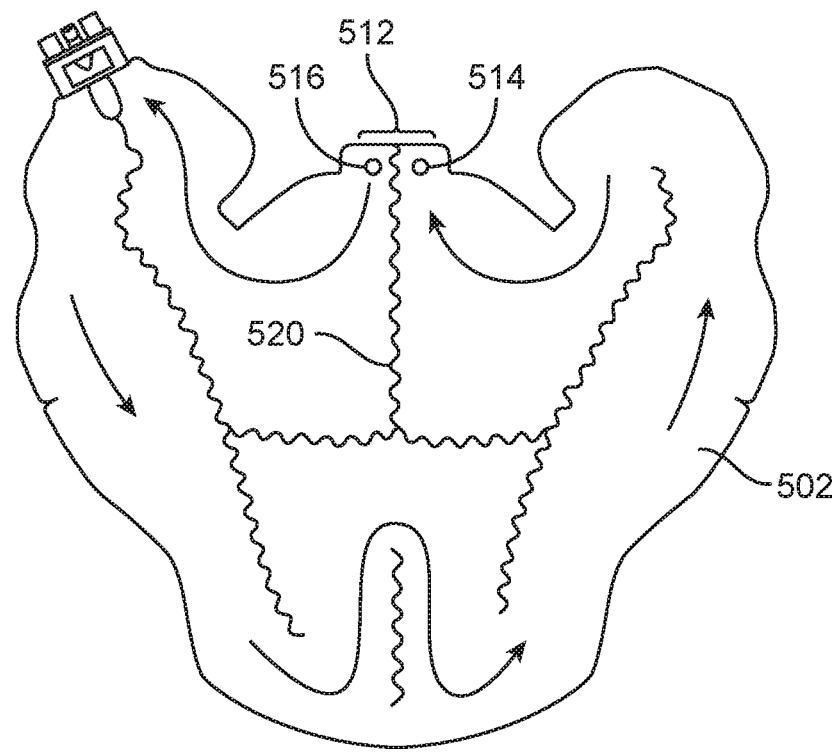
FIGS. 5A-5C illustrate an alternative embodiment of a multi-sectional therapy wrap.
Figure 5B:
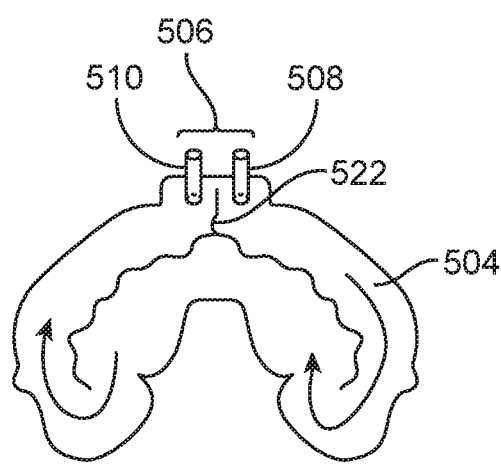
Figure 5C:
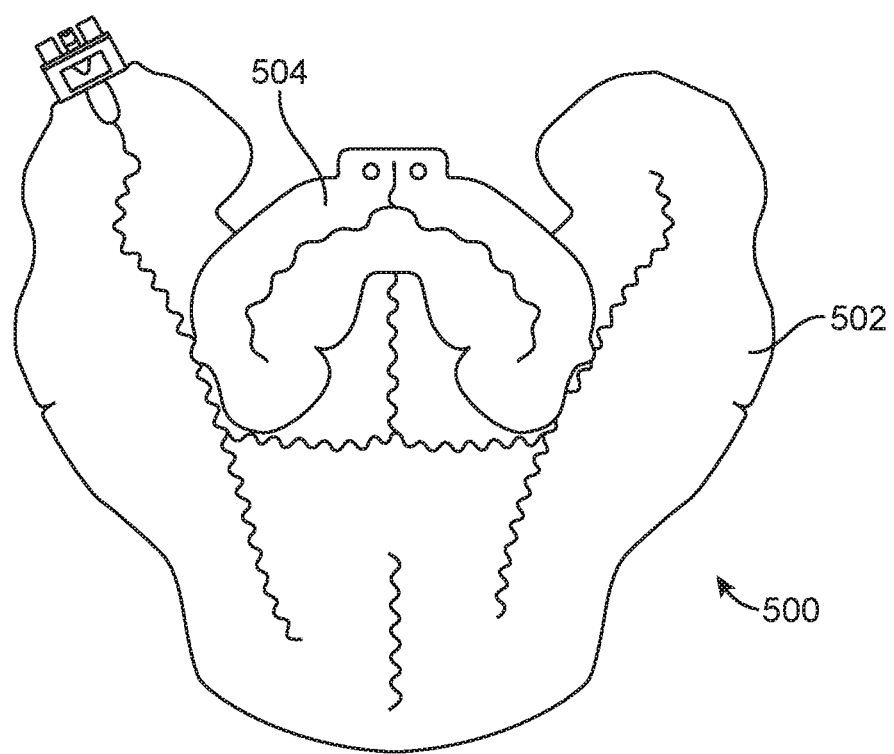

FIGS. 5A-5C illustrate an alternative embodiment of a multi-sectional therapy wrap 500 similar to the embodiments described above. However, instead of having a fluid junction as described above for joining the wrap sections, the first wrap section 502 can be joined to the second wrap section 504 using a fluid connector 506 comprising a first port 508 and a second port 510, where one port is an inlet port and the other port is an outlet port. In the illustrated embodiment, the fluid connector 506 is located on the second wrap section. However, in other embodiments, the fluid connector can be located on any other wrap section. Also, as illustrated, the first port 508 serves and the inlet port and the second port 510 serves as the outlet port for the second wrap section 504. In other embodiments, the fluid flow can be reversed, making the first port 508 an outlet port and the second port 510 an inlet port.

The fluid connector 506 can be joined to a receptacle 512 than can have complementary receiving ports 514, 516 for receiving and forming a fluid tight seal with the first port 508 and second 510. For example, the fluid connector 506 can have male fluid ports while the receptacle 512 can have complementary female fluid ports. Alternatively, the fluid connector 506 can have female fluid ports while the receptacle 508 can have male fluid ports.

To ensure proper flow through the wrap sections, the placement of interior fences, as described above, can be used to form a unidirectional flow path through the wrap sections. For example, the first wrap section 502 can have one or more interior fences 520 that extend from the fluid manifold 518 that defines a fluid flow path through the first wrap section, and the second wrap section 504 can also have one or more interior fences 522 that define a fluid flow path through the second wrap section. These fluid fences can be similarly arranged for a similar function as the fences described above.

One interior fence 522 of the second wrap section 504 can divide the fluid connector 506 into two portions, with one portion having the first port 508 and the second oprtion having the second port 510. For example, one interior fence 522 can extend between the first port 508 and the second portion 510 to form a fluid path that forces the fluid to traverse the entire wrap section as it moves from one port to the other port.

Similarly, an interior fence 520 of the first wrap section 502 can divide the receptacle 512 into two portions with one portion having one receiving port 514 and the second portion having the other receiving port 516. In this wrap section, the interior fence 520 can extend between the two receiving ports 514, 516 to form a fluid path that forces the fluid to traverse the leave the first wrap section 502 and traverse the entire second wrap section 504 before it returns to the first wrap section 502 to complete its path through the first wrap section 502.

In some embodiments, the attachment of the fluid connector 506 to the receptacle 512 can be reversible, which allows various wrap sections to be modularly joined together according to the needs of the patient. In other embodiments, the attachment of the fluid connector 506 to the receptacle 512 can be made permanent.

In some embodiments, the ports can be tubular or circular as shown, while in other embodiments, the ports can be rectangular, square, or have a geometry that corresponds to the shape of the fluid flow path at the fluid connector or receptacle.

Figure 6A:
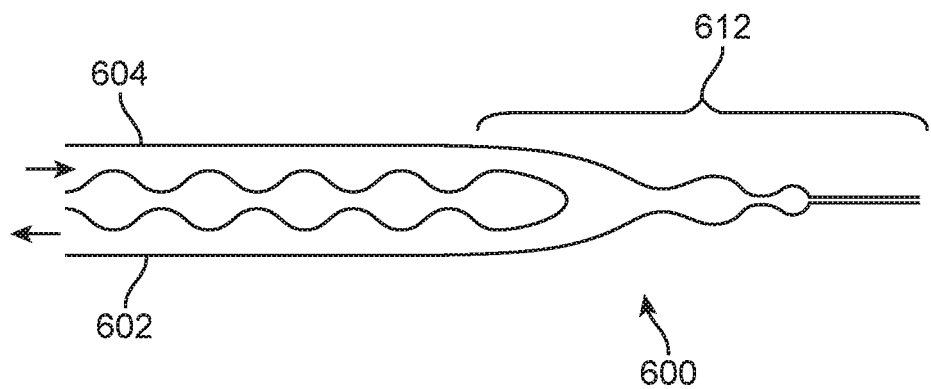
FIGS. 6A-6B illustrate an example of a potential blockage that may occur in or around the junction between two wrap sections.
Figure 6B:
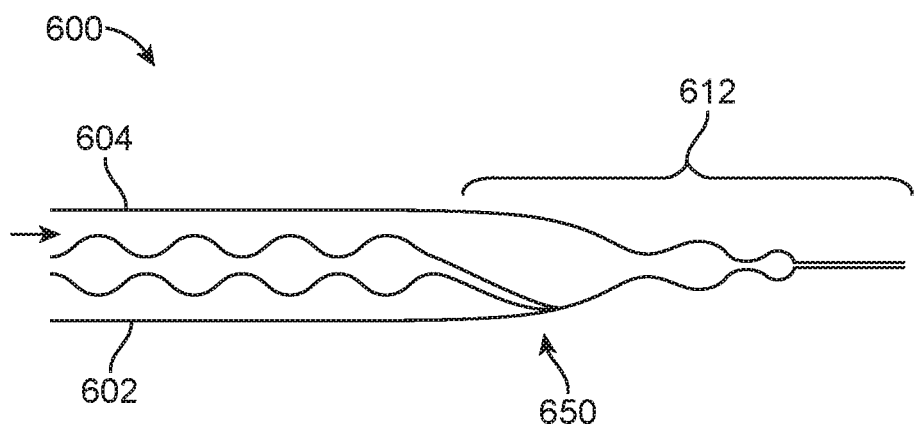
Figure 7A:
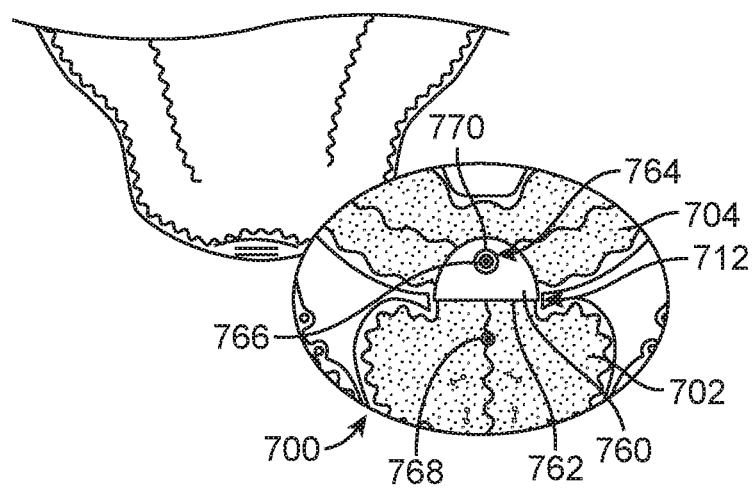
FIGS. 7A-7D illustrate an embodiment of a spacer that can be inserted between two wrap sections near or at the junction to reduce blockages within the junction area.
Figure 7B:
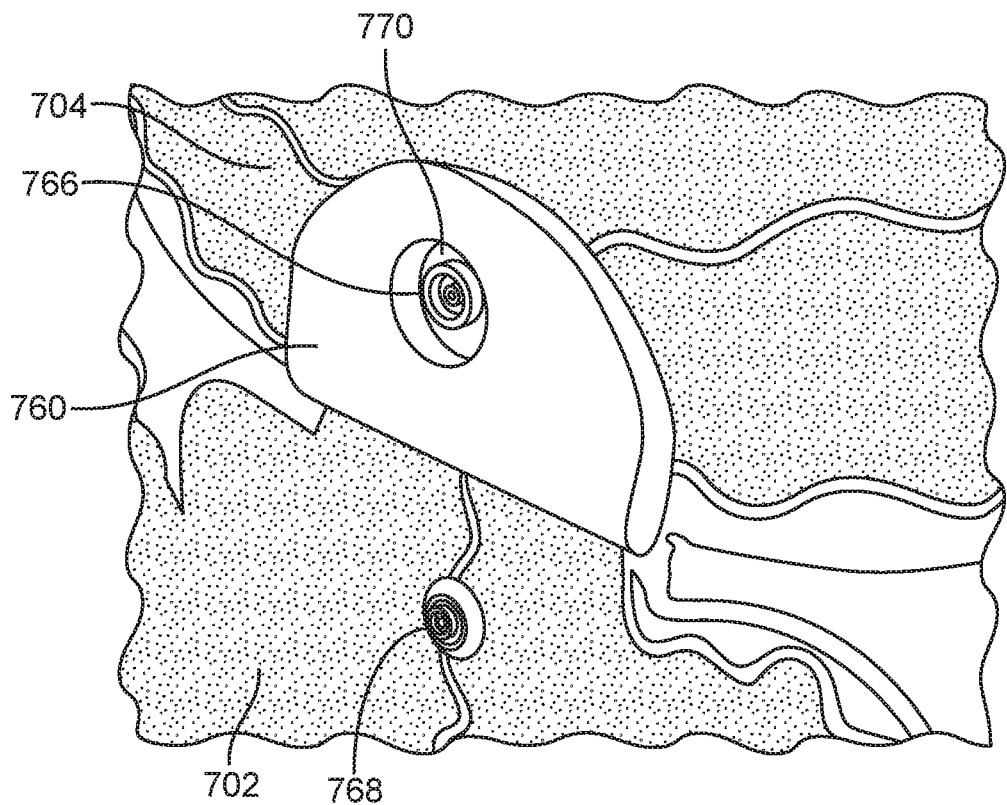
Figure 7C:
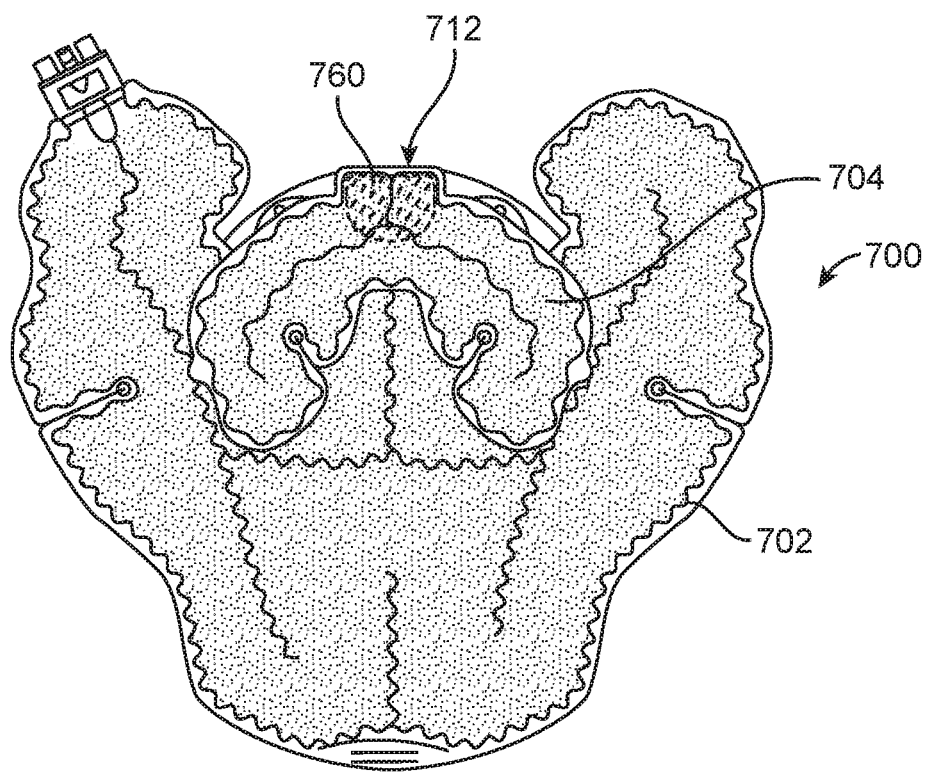
Figure 7D:
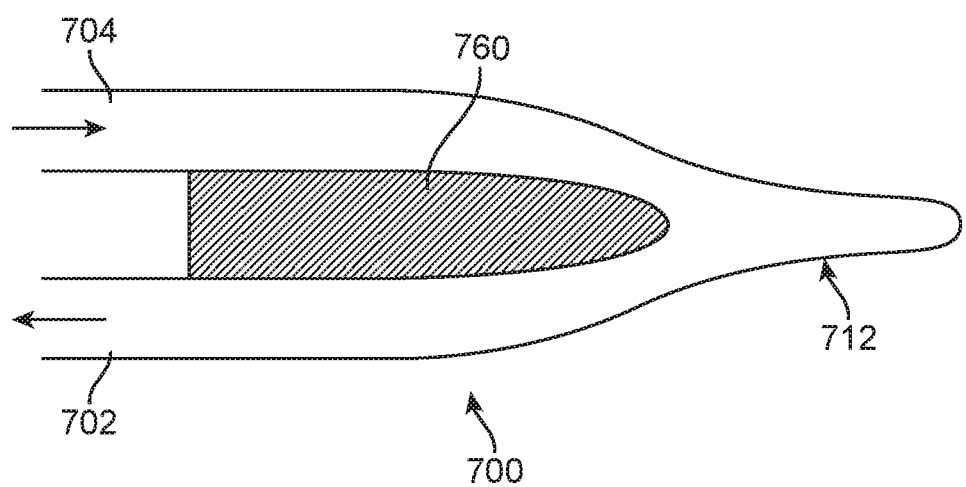

FIGS. 6A and 6B illustrate a potential blockage point around the junction 612 of a multi-sectional therapy wrap 600 that connects a first wrap section 602 with a second wrap section 604. This blockage may occur as the flow of fluid passes from one wrap section into the junction 612, particularly when the wrap section only is made from a single fluid layer, such as a neck wrap formed from a single fluid layer. As the fluid passes from the wrap section to the junction, the fluid may push down a portion of the bladder wall to form a blockage 650 that can impede fluid flow through the therapy wrap 600.

FIG. 7A-7D illustrate one embodiment of a spacer 760 that can be positioned at the junction 712 of the multi-sectional therapy wrap 700 between the exterior fluid sides of both the first wrap section 702 and the second wrap section 704. The spacer 760 can provide separation and support to the layers around the junction 712 that prevents or reduces the likelihood of formation of the blockage. The spacer 760 can be about the same width as the junction 712 and can have at least one straight side 762 that can abut against the junction 712. The junction 712 can otherwise have various shapes, such as the half circle shown, or be square or rectangular. An adhesive can be used to attach the spacer 760 to one of the wrap sections, such as the neck wrap section. In addition, a fastener 764, such as a button type fastener formed from a socket 766 and stud 768, can be used reversibly secure the spacer 760 against the other wrap section in the proper configuration. The fastener 764 can be placed through an opening 770 in the spacer 760. One part of the fastener 764, such as the socket 766, can be placed on one of the wrap sections near the junction 712, and the other part of the fastener 764, such as the stud 768, can be placed on an opposing portion of the other wrap section. The spacer 760 can be placed on one of the wrap sections by aligning the opening 770 with one of the fastener 764 parts, either the socket 766 or stud 768. The fastener connection to the bladder can be made leak free by welding one or more perimeter shapes, such as a circle or concentric circles, around the fastener 764 to prevent leaks between the fastener location and the bladder. The weld may be performed during the welding of the main body and neck weld operations, or may be done at once, during the junction weld to ensure proper registration. The spacer may be sufficiently thick so as to allow the fastener to be sublet below the surface of the spacer, thus protecting the body from uncomfortable contact with the fastener. In other words, in some embodiments, the spacer 760 may by thicker than the height of the fastener 764.

In some embodiments, the spacer 760 can be made of foam or a gel pad or some other material that provides both physical support, can provide spacing between the wrap sections, and is compliant or resilient so that the therapy wrap can be conformed against the patient's skin. In some embodiments, the spacer 760 can be between about 2 mm to 20 mm in thickness.

Figure 8A:
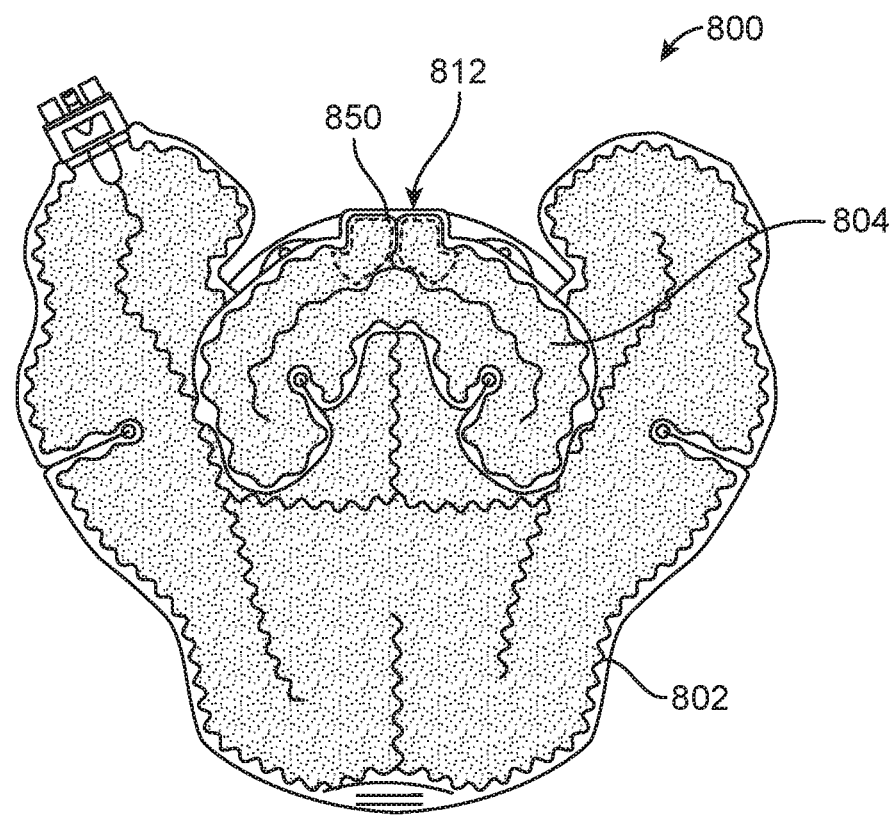
FIGS. 8A and 8B illustrate an embodiment of a shunt or stent that can be disposed within the junction to prevent blockages within the junction area.
Figure 8B:
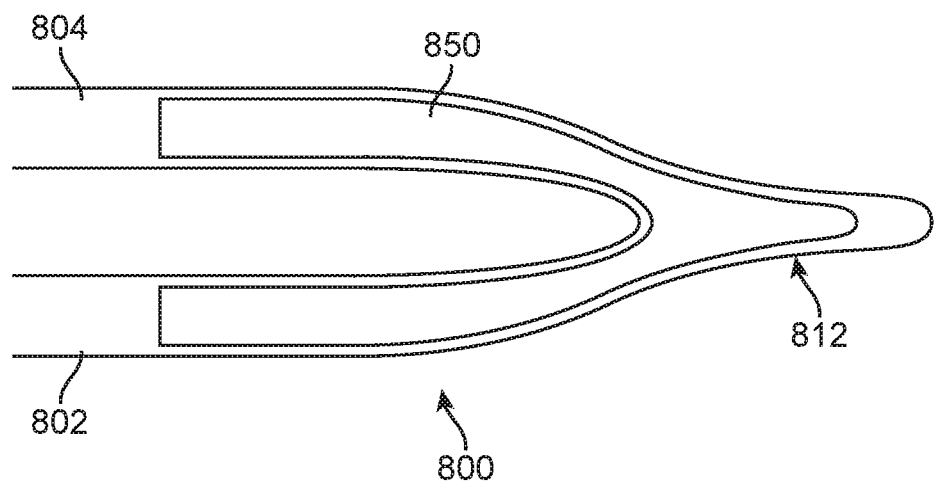

FIGS. 8A and 8B illustrates an embodiment of a shunt 850 or stent that can be inserted into the junction 812 of the therapy wrap to ensure that flow between the first wrap section 802 and second wrap section 804 is not impeded. The shunt 850 can be a structural member with a lumen that props open the channels within the junction 812 and surrounding portions of the wrap sections. The shunt 850 can be tubular or have a cross-sectional profile that matches the shape of the fluid channel in which it is disposed. The shunt 850 can be U shaped to provide structural support from the first wrap section 802, through the junction 812, and to the second wrap section 804. Unlike the spacer 760 which remains outside the fluid channels of the wrap sections, the shunt 850 is disposed within the fluid channels to provide additional structural support to the fluid channels. A shunt 850 can be disposed within each half of the junction 812 to provide complete support to the junction 812.

Other structures and devices can also be used to prevent kinking or blockage at the junction area between two wrap sections. For example, a snap or clasp can be placed over the junction to hold the junction to a particular shape and to prevent kinking at the junction. Alternatively, the junction and portions of the wrap sections adjacent the junction can be made of structurally stiffer materials, or reinforcing members or layers can be added to increase the stiffness, relative to other portions of the therapy wrap.

The multi-sectional therapy wraps described herein can be used to treat body parts with a relative complex geometry, such as the foot and ankle region, the head and neck region, the shoulder region, the pelvic region, and the like. In some embodiments, the therapy wrap may have three or more wrap sections. In some embodiments, each of the wrap sections can be fluidically connected to one of the other wrap sections, thereby allowing the entire therapy wrap to be supplied with fluid using a single fluid manifold located on one of the wrap sections.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

What is claimed is:

1. A multi-sectional therapy wrap, the therapy wrap comprising:
    a first wrap section comprising a first fluid bladder, the first fluid bladder having a first interior fence that defines a first fluid flow path through the first fluid bladder, and the first wrap section being defined by a first perimeter fence;
    a second wrap section comprising a second fluid bladder, the second fluid bladder having a second interior fence that defines a second fluid flow path through the second fluid bladder, the second wrap section being defined by a second perimeter fence, wherein the second wrap section overlaps at least a portion of the first wrap section;
    an air bladder covering only the first fluid bladder;
    a junction connecting the first fluid bladder of the first wrap section with the second fluid bladder of the second wrap sections, the junction partitioned into a first portion and a second portion with a third interior fence, wherein the third interior fence is aligned with both the first interior fence and the second interior fence to integrate the first fluid flow path with the second fluid flow path,
        wherein the first fluid bladder is formed from first, second, and third sheets of material, the first and second sheets of material being welded together to form a first portion of the first perimeter fence, and the first and third sheets of material being welded together to form a second portion of the first perimeter fence,
        wherein portions of the second and third sheets of material extend beyond the junction and are welded together to form the second perimeter fence,
        wherein each of the first and second perimeter fences have a gap formed therein for the junction, and
        wherein the air bladder comprises a fourth sheet of material that is welded to the first and second sheets of material along the first portion of the first perimeter fence and to the first and third sheets of material along the second portion of the first perimeter fence, such that the first sheet of material is internal to the first wrap section.

2. The therapy wrap of claim 1, wherein the first fluid bladder comprises attachment points that are configured to limit expansion of the first fluid bladder and facilitate fluid flow through the first fluid bladder.

3. The therapy wrap of claim 2, wherein the second fluid bladder comprises attachment points that are configured to limit the expansion of the second fluid bladder and facilitate fluid flow through the second fluid bladder.

4. The therapy wrap of claim 3, wherein the attachment points configured to limit expansion of the second fluid bladder have a larger diameter than the attachment points configured to limit expansion of the first fluid bladder.

5. The therapy wrap of claim 3, wherein the attachment points to limit expansion of the second fluid bladder are spaced farther apart than the attachment points configured to limit expansion of the first fluid bladder.

6. The therapy wrap of claim 1, further comprising a manifold in fluid communication with the first wrap section, the manifold comprising a fluid inlet and a fluid outlet in fluid communication with the first fluid bladder.

7. The therapy wrap of claim 6, wherein the first interior fence extends from the manifold to divide a portion of the first fluid bladder adjacent the manifold into a fluid outflow tract and a fluid inflow tract.

8. The therapy wrap of claim 1, further comprising a spacer disposed between the first wrap section and the second wrap section and adjacent the junction.

9. The therapy wrap of claim 8, the spacer being positioned at the junction between an exterior side of both the first wrap section and the second wrap section.

10. The therapy wrap of claim 1, wherein the second wrap section comprises a curved biasing element adapted to bias the second wrap section against a patient's neck.

11. The therapy wrap of claim 1, wherein the first wrap section comprises one or more inserts adapted to maintain the shape of the first wrap section against compression.

12. The therapy wrap of claim 1, further comprising one or more shunts disposed within the junction, wherein the one or more shunts are configured to prevent or reduce the likelihood of kinking in the junction.

13. A multi-sectional therapy wrap, the therapy wrap comprising:
    a first wrap section comprising a first fluid bladder, the first fluid bladder having a first interior fence that defines a first fluid flow path through the first fluid bladder, the first fluid bladder having a fluid connector comprising a first port and a second port, wherein the first interior fence divides the fluid connector and separates the first port from the second port, and the first wrap section being defined by a first perimeter fence;
    an air bladder covering only the first fluid bladder;
    a second wrap section comprising a second fluid bladder, the second fluid bladder having a second interior fence that defines a second fluid flow path through the second fluid bladder, the second fluid bladder having a receptacle comprising a first receiving port and a second receiving port, wherein the second interior fence divides the receptacle and separates the first receiving port and the second receiving port, and the second wrap being defined by a second perimeter fence;
    wherein the fluid connector is fluidically coupled to the receptacle to allow fluid to flow between the first wrap section and the second wrap section,
    wherein the first fluid bladder is formed from first, second, and third sheets of material, the first and second sheets of material being welded together to form a first portion of the first perimeter fence, and the first and third sheets of material being welded together to form a second portion of the first perimeter fence,
    wherein portions of the second and third sheets of material extend beyond the fluid connector and are welded together to form the second perimeter fence,
    wherein each of the first and second perimeter fences have a gap formed therein for the fluid connector, and
    wherein the air bladder comprises a fourth sheet of material that is welded to the first and second sheets of material along the first portion of the first perimeter fence and to the first and third sheets of material along the second portion of the first perimeter fence, such that the first sheet of material is internal to the first wrap section.

14. The therapy wrap of claim 13, wherein the fluid connector is reversibly coupled to the receptacle.

15. The therapy wrap of claim 13, wherein the fluid connector is permanently coupled to the receptacle.

16. The therapy wrap of claim 13, wherein in use the fluid flow between the first wrap section and the second wrap section is flowing between the first port and the first receiving port and between the second port and the second receiving port, a perimeter fence coupled to and disposed around perimeters of the first fluid bladder, the second fluid bladder, and the air bladder.

17. A multi-sectional therapy wrap, the therapy wrap comprising:
   a first wrap section comprising a first fluid bladder and a gas bladder operable only on a first fluid bladder, the first fluid bladder having a first interior fence that defines a first fluid flow path through the first fluid bladder, and the first wrap section being defined by a first perimeter fence;
   a second wrap section comprising a second fluid bladder, the second fluid bladder having a second interior fence that defines a second fluid flow path through the second fluid bladder, the second wrap section being defined by a second perimeter fence, wherein the second wrap section overlaps at least a portion of the first wrap section; and
   a junction connecting the first fluid bladder of the first wrap section with the second fluid bladder of the second wrap sections, the junction partitioned into a first portion and a second portion with a third interior fence, wherein the third interior fence is aligned with both the first interior fence and the second interior fence to integrate the first fluid flow path with the second fluid flow path,
   wherein the first fluid bladder is formed from first, second, and third sheets of material, the first and second sheets of material being welded together to form a first portion of the first perimeter fence, and the first and third sheets of material being welded together to form a second portion of the first perimeter fence,
   wherein portions of the second and third sheets of material extend beyond the junction and are welded together to form the second perimeter fence,
   wherein each of the first and second perimeter fences have a gap therein for the junction.

18. The therapy wrap of claim 17, further comprising a manifold in fluid communication with the first wrap section, the manifold comprising a fluid inlet and a fluid outlet in fluid communication with the first fluid bladder, and a gas line in communication with the gas bladder.

* * * * *

UNITED STATES PATENT AND TRADEMARK OFFICE
CERTIFICATE OF CORRECTION

| | | |
|---|---|---|
| PATENT NO. | : 11,672,693 B2 | Page 1 of 1 |
| APPLICATION NO. | : 16/178467 | |
| DATED | : June 13, 2023 | |
| INVENTOR(S) | : Tamara L. Hilton et al. | |

It is certified that error appears in the above-identified patent and that said Letters Patent is hereby corrected as shown below:

In the Claims

In Column 16, Line 21 of Claim 17, the text, "...a gap therein for the junction." should read,
-- a gap formed therein for the junction. --

Signed and Sealed this
First Day of August, 2023

Katherine Kelly Vidal
Director of the United States Patent and Trademark Office